United States Patent
Macpherson et al.

(10) Patent No.: US 11,468,971 B2
(45) Date of Patent: *Oct. 11, 2022

(54) ANCESTRY FINDER

(71) Applicant: 23andMe, Inc., Sunnyvale, CA (US)

(72) Inventors: John Michael Macpherson, Santa Ana, CA (US); Brian Thomas Naughton, Mountain View, CA (US); Joanna Louise Mountain, Menlo Park, CA (US)

(73) Assignee: 23andMe, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/077,930

(22) Filed: Oct. 22, 2020

(65) Prior Publication Data

US 2021/0043281 A1 Feb. 11, 2021

Related U.S. Application Data

(63) Continuation of application No. 15/664,619, filed on Jul. 31, 2017, now Pat. No. 10,854,318, which is a (Continued)

(51) Int. Cl.
*G16B 50/30* (2019.01)
*G06F 16/2457* (2019.01)
(Continued)

(52) U.S. Cl.
CPC ......... *G16B 50/30* (2019.02); *G06F 16/2457* (2019.01); *G06F 16/9535* (2019.01);
(Continued)

(58) Field of Classification Search
CPC ........ G16B 30/00; G16B 20/00; G16B 20/10; G16B 40/00; G16B 50/00; G16B 20/20;
(Continued)

(56) References Cited

U.S. PATENT DOCUMENTS 5,376,526 A 12/1994 Brown et al.
5,551,880 A 9/1996 Bonnstetter et al.
(Continued)

FOREIGN PATENT DOCUMENTS

EP 0 967 291 A1 12/1999
WO WO-0210456 A2 2/2002
(Continued)

OTHER PUBLICATIONS

Meuwissen T.H.E. et al. Prediction of identity by descent probabilities from marker haplotypes. 2001 Genet Sel Evol. vol. 33, p. 605-634; cited in a parent application. (Year: 2001).*

(Continued)

*Primary Examiner* — Mary K Zeman
(74) *Attorney, Agent, or Firm* — Weaver Austin Villeneuve & Sampson LLP; David K. Buckingham

(57) ABSTRACT

Inferring a characteristic of an individual is disclosed. An indication that a first user and a second user have at least one shared chromosomal segment is received. Information about the second user is obtained. A characteristic of the first user is inferred based at least in part on the information about the second user.

25 Claims, 24 Drawing Sheets
(11 of 24 Drawing Sheet(s) Filed in Color)

Related U.S. Application Data continuation of application No. 12/774,546, filed on May 5, 2010, now abandoned, which is a continuation-in-part of application No. 12/644,791, filed on Dec. 22, 2009, now Pat. No. 8,463,554.

(60) Provisional application No. 61/204,195, filed on Dec. 31, 2008.

(51) Int. Cl.
    *G06F 16/9535*     (2019.01)
    *G16B 50/00*     (2019.01)
    *G16B 10/00*     (2019.01)
    *G16B 30/00*     (2019.01)
    *G06N 5/04*     (2006.01)

(52) U.S. Cl.
    CPC .............. *G06N 5/048* (2013.01); *G16B 10/00* (2019.02); *G16B 30/00* (2019.02); *G16B 50/00* (2019.02)

(58) Field of Classification Search
CPC ........ G16B 30/10; G16B 40/20; G16B 25/00; G16B 50/30; G16B 15/00; G16B 30/20; G16B 40/30; G16B 50/40; G16B 10/00; G16B 20/40; G16B 45/00; G16B 5/20; G16B 50/10; G16B 5/00; G16B 50/20; G06F 16/29; G06F 16/248; G06F 21/84; G06F 16/21; G06F 16/35; G06F 16/43; G06F 16/909; G06F 16/9535; G06F 17/11; G06F 17/16; G06F 17/18; G06F 16/2457; G06F 16/2246; G06F 16/24558; G06F 16/24564; G06F 16/24578; G06F 16/285; G06F 16/288; G06N 20/00; G06N 3/08; G06N 7/005; G06N 3/0454; G06N 5/04; G06N 5/046; G06N 20/20; G06N 3/088; G06N 5/003; G06N 5/025; G06N 7/00; G06K 9/6256; G06K 9/6228; G06K 9/6215; G06K 9/6218; G06K 9/6221; G06K 9/6223; G06K 9/6227; G06K 9/6261; G06K 9/6262; G06K 9/6289; G06T 7/60; G06T 11/00; G06T 11/206; G06T 11/60; G06T 2207/10024; G06T 7/143; G06T 7/32; G06T 7/77; G16H 10/60; G16H 50/20; G16H 50/30; G16H 10/40; G16H 15/00; G16H 50/70; G16H 10/20; G16H 80/00; G06Q 10/0635; G06Q 10/063114; C12Q 2600/156; C12Q 2600/172; C12Q 2600/124

See application file for complete search history.

(56) References Cited

U.S. PATENT DOCUMENTS

| | | |
|---|---|---|
| 5,649,181 A | 7/1997 | French et al. |
| 5,660,176 A | 8/1997 | Iliff |
| 5,692,501 A | 12/1997 | Minturn |
| 5,752,242 A | 5/1998 | Havens |
| 5,769,074 A | 6/1998 | Barnhill et al. |
| 5,839,120 A | 11/1998 | Thearling |
| 5,940,802 A | 8/1999 | Hildebrand et al. |
| 5,985,559 A | 11/1999 | Brown |
| 6,063,028 A | 5/2000 | Luciano |
| 6,108,647 A | 8/2000 | Poosala et al. |
| 6,131,092 A | 10/2000 | Masand |
| 6,203,993 B1 | 3/2001 | Shuber et al. |
| 6,216,134 B1 | 4/2001 | Heckerman et al. |
| 6,253,203 B1 | 6/2001 | O'Flaherty et al. |
| 6,269,364 B1 | 7/2001 | Kennedy et al. |
| 6,321,163 B1 | 11/2001 | Graham et al. |
| 6,393,399 B1 | 5/2002 | Even |
| 6,487,541 B1 | 11/2002 | Aggarwal et al. |
| 6,493,637 B1 | 12/2002 | Steeg |
| 6,506,562 B1 | 1/2003 | Weissman et al. |
| 6,507,840 B1 | 1/2003 | Ioannidis et al. |
| 6,519,604 B1 | 2/2003 | Acharya et al. |
| 6,601,059 B1 | 7/2003 | Fries |
| 6,629,097 B1 | 9/2003 | Keith |
| 6,629,935 B1 | 10/2003 | Miller et al. |
| 6,640,211 B1 | 10/2003 | Holden |
| 6,687,696 B2 | 2/2004 | Hofmann et al. |
| 6,694,311 B1 | 2/2004 | Smith |
| 6,730,023 B1 | 5/2004 | Dodds |
| 6,738,762 B1 | 5/2004 | Chen et al. |
| 6,873,914 B2 | 3/2005 | Winfield et al. |
| 6,887,666 B1 | 5/2005 | Hager |
| 6,912,492 B1 | 6/2005 | Johnson et al. |
| 6,931,326 B1 | 8/2005 | Judson et al. |
| 6,994,962 B1 | 2/2006 | Thilly |
| 7,054,758 B2 | 5/2006 | Gill-Garrison et al. |
| 7,062,752 B2 | 6/2006 | Simpson et al. |
| 7,069,308 B2 | 6/2006 | Abrams |
| 7,072,794 B2 | 7/2006 | Wittkowski |
| 7,107,155 B2 | 9/2006 | Frudakis |
| 7,127,355 B2 | 10/2006 | Cox et al. |
| 7,162,471 B1 | 1/2007 | Knight et al. |
| 7,271,243 B2 | 9/2007 | Dumas et al. |
| 7,366,719 B2 | 4/2008 | Shaw |
| 7,461,006 B2 | 12/2008 | Gogolak |
| 7,572,603 B2 | 8/2009 | Small et al. |
| 7,592,910 B2 | 9/2009 | Tuck et al. |
| 7,720,855 B2 | 5/2010 | Brown |
| 7,739,247 B2 | 6/2010 | Mount et al. |
| 7,752,215 B2 | 7/2010 | Dettinger et al. |
| 7,788,358 B2 | 8/2010 | Martino |
| 7,797,302 B2 | 9/2010 | Kenedy et al. |
| 7,818,310 B2 | 10/2010 | Kenedy et al. |
| 7,844,609 B2 | 11/2010 | Kenedy et al. |
| 7,877,398 B2 | 1/2011 | Kroeschel et al. |
| 7,904,511 B2 | 3/2011 | Ryan et al. |
| 7,917,374 B2 | 3/2011 | Walker |
| 7,917,438 B2 | 3/2011 | Kenedy et al. |
| 7,930,156 B2 | 4/2011 | Maruhashi et al. |
| 7,933,912 B2 | 4/2011 | Kenedy et al. |
| 7,941,329 B2 | 5/2011 | Kenedy et al. |
| 7,941,434 B2 | 5/2011 | Kenedy et al. |
| 7,951,078 B2 | 5/2011 | Scheuner |
| 7,957,907 B2 | 6/2011 | Sorenson et al. |
| 7,996,157 B2 | 8/2011 | Zabeau et al. |
| 8,024,348 B2 | 9/2011 | Kenedy et al. |
| 8,051,033 B2 | 11/2011 | Kenedy et al. |
| 8,055,643 B2 | 11/2011 | Kenedy et al. |
| 8,065,324 B2 | 11/2011 | Kenedy et al. |
| 8,073,708 B1 | 12/2011 | Igoe et al. |
| 8,099,424 B2 | 1/2012 | Kenedy et al. |
| 8,108,406 B2 | 1/2012 | Kenedy et al. |
| 8,185,461 B2 | 5/2012 | Kenedy et al. |
| 8,187,811 B2 | 5/2012 | Eriksson et al. |
| 8,200,509 B2 | 6/2012 | Kenedy et al. |
| 8,209,319 B2 | 6/2012 | Kenedy et al. |
| 8,224,835 B2 | 7/2012 | Kenedy et al. |
| 8,255,403 B2 | 8/2012 | Kenedy et al. |
| 8,326,648 B2 | 12/2012 | Kenedy et al. |
| 8,386,519 B2 | 2/2013 | Kenedy et al. |
| 8,428,886 B2 | 4/2013 | Wong et al. |
| 8,452,619 B2 | 5/2013 | Kenedy et al. |
| 8,458,097 B2 | 6/2013 | Kenedy et al. |
| 8,458,121 B2 | 6/2013 | Kenedy et al. |
| 8,463,554 B2 * | 6/2013 | Hon .................... G06F 16/2457 702/19 |
| 8,510,057 B1 | 8/2013 | Avey et al. |
| 8,543,339 B2 | 9/2013 | Wojcicki et al. |
| 8,589,437 B1 | 11/2013 | Khomenko et al. |
| 8,606,761 B2 | 12/2013 | Kenedy et al. |
| 8,635,087 B1 | 1/2014 | Igoe et al. |
| 8,645,343 B2 | 2/2014 | Wong et al. |
| 8,655,899 B2 | 2/2014 | Kenedy et al. |

(56) References Cited

U.S. PATENT DOCUMENTS

| | | | |
|---|---|---|---|
| 8,655,908 B2 | 2/2014 | Kenedy et al. |
| 8,655,915 B2 | 2/2014 | Kenedy et al. |
| 8,719,045 B2 | 5/2014 | Yoon et al. |
| 8,738,297 B2 | 5/2014 | Sorenson et al. |
| 8,786,603 B2 | 7/2014 | Rasmussen et al. |
| 8,788,283 B2 | 7/2014 | Kenedy et al. |
| 8,788,286 B2 | 7/2014 | Kenedy et al. |
| 8,855,935 B2* | 10/2014 | Myres | G16B 20/00 702/19 |
| 8,990,250 B1 | 3/2015 | Chowdry et al. |
| 9,031,870 B2 | 5/2015 | Kenedy et al. |
| 9,116,882 B1 | 8/2015 | Macpherson et al. |
| 9,170,992 B2 | 10/2015 | Kenedy et al. |
| 9,213,944 B1 | 12/2015 | Do et al. |
| 9,213,947 B1 | 12/2015 | Do et al. |
| 9,218,451 B2 | 12/2015 | Wong et al. |
| 9,336,177 B2 | 5/2016 | Hawthorne et al. |
| 9,367,663 B2 | 6/2016 | Deciu et al. |
| 9,367,800 B1* | 6/2016 | Do | G06N 20/00 |
| 9,390,225 B2 | 7/2016 | Barber et al. |
| 9,405,818 B2 | 8/2016 | Chowdry et al. |
| 9,582,647 B2 | 2/2017 | Kenedy et al. |
| 9,836,576 B1 | 12/2017 | Do et al. |
| 9,864,835 B2 | 1/2018 | Avey et al. |
| 9,977,708 B1 | 5/2018 | Do et al. |
| 10,025,877 B2 | 7/2018 | Macpherson |
| 10,162,880 B1 | 12/2018 | Chowdry et al. |
| 10,275,569 B2 | 4/2019 | Avey et al. |
| 10,296,847 B1* | 5/2019 | Do | G06N 5/022 |
| 10,379,812 B2 | 8/2019 | Kenedy et al. |
| 10,432,640 B1 | 10/2019 | Hawthorne et al. |
| 10,437,858 B2 | 10/2019 | Naughton et al. |
| 10,516,670 B2 | 12/2019 | Hawthorne et al. |
| 10,572,831 B1* | 2/2020 | Do | G16B 20/00 |
| 10,643,740 B2 | 5/2020 | Avey et al. |
| 10,658,071 B2 | 5/2020 | Do et al. |
| 10,691,725 B2 | 6/2020 | Naughton et al. |
| 10,699,803 B1* | 6/2020 | Do | G16B 40/00 |
| 10,755,805 B1 | 8/2020 | Do et al. |
| 10,777,302 B2 | 9/2020 | Chowdry et al. |
| 10,790,041 B2 | 9/2020 | Macpherson et al. |
| 10,803,134 B2 | 10/2020 | Kenedy et al. |
| 10,841,312 B2 | 11/2020 | Hawthorne et al. |
| 10,854,318 B2* | 12/2020 | Macpherson | G06F 16/9535 |
| 10,891,317 B1 | 1/2021 | Chowdry et al. |
| 10,896,233 B2 | 1/2021 | Kenedy et al. |
| 10,936,626 B1 | 3/2021 | Naughton et al. |
| 10,957,455 B2 | 3/2021 | Kenedy et al. |
| 10,991,467 B2 | 4/2021 | Kenedy et al. |
| 10,999,285 B2 | 5/2021 | Hawthorne et al. |
| 11,003,694 B2 | 5/2021 | Kenedy et al. |
| 11,031,101 B2 | 6/2021 | Hon et al. |
| 11,049,589 B2 | 6/2021 | Hon et al. |
| 11,170,047 B2 | 11/2021 | Macpherson |
| 11,170,873 B2 | 11/2021 | Avey et al. |
| 11,171,962 B2 | 11/2021 | Hawthorne et al. |
| 11,322,227 B2 | 5/2022 | Hon et al. |
| 2001/0000810 A1 | 5/2001 | Alabaster |
| 2002/0010552 A1 | 1/2002 | Rienhoff, Jr. et al. |
| 2002/0019746 A1 | 2/2002 | Rienhoff, Jr. et al. |
| 2002/0048763 A1 | 4/2002 | Penn et al. |
| 2002/0052697 A1 | 5/2002 | Serita |
| 2002/0052761 A1 | 5/2002 | Fey et al. |
| 2002/0077775 A1 | 6/2002 | Schork et al. |
| 2002/0094532 A1 | 7/2002 | Bader et al. |
| 2002/0120623 A1 | 8/2002 | Vivier et al. |
| 2002/0123058 A1 | 9/2002 | Threadgill et al. |
| 2002/0126545 A1 | 9/2002 | Warren et al. |
| 2002/0128860 A1 | 9/2002 | Leveque et al. |
| 2002/0133299 A1 | 9/2002 | Jacob et al. |
| 2002/0137086 A1 | 9/2002 | Olek et al. |
| 2002/0138572 A1 | 9/2002 | Delany et al. |
| 2002/0156043 A1 | 10/2002 | Pfost |
| 2002/0161664 A1 | 10/2002 | Shaya et al. |
| 2002/0169793 A1 | 11/2002 | Sweeney |
| 2002/0174096 A1 | 11/2002 | O'Reilly et al. |
| 2002/0179097 A1 | 12/2002 | Atkins |
| 2002/0183965 A1 | 12/2002 | Gogolak |
| 2003/0009295 A1 | 1/2003 | Markowitz et al. |
| 2003/0030637 A1 | 2/2003 | Grinstein et al. |
| 2003/0040002 A1 | 2/2003 | Ledley |
| 2003/0046114 A1 | 3/2003 | Davies et al. |
| 2003/0065241 A1 | 4/2003 | Hohnloser |
| 2003/0065535 A1 | 4/2003 | Karlov et al. |
| 2003/0101000 A1 | 5/2003 | Bader et al. |
| 2003/0113727 A1 | 6/2003 | Girn et al. |
| 2003/0130873 A1 | 7/2003 | Nevin et al. |
| 2003/0135096 A1 | 7/2003 | Dodds |
| 2003/0135488 A1 | 7/2003 | Amir et al. |
| 2003/0165926 A1 | 9/2003 | Olek et al. |
| 2003/0167260 A1 | 9/2003 | Nakamura et al. |
| 2003/0171876 A1 | 9/2003 | Markowitz et al. |
| 2003/0172065 A1 | 9/2003 | Sorenson et al. |
| 2003/0195706 A1 | 10/2003 | Korenberg |
| 2003/0198970 A1 | 10/2003 | Roberts |
| 2003/0203370 A1 | 10/2003 | Yakhini et al. |
| 2003/0204418 A1 | 10/2003 | Ledley |
| 2003/0212579 A1 | 11/2003 | Brown et al. |
| 2003/0224394 A1 | 12/2003 | Schadt et al. |
| 2003/0233377 A1 | 12/2003 | Kovac |
| 2004/0002816 A1 | 1/2004 | Milosavljevic |
| 2004/0006488 A1 | 1/2004 | Fitall et al. |
| 2004/0009495 A1 | 1/2004 | O'Malley et al. |
| 2004/0014097 A1 | 1/2004 | McGlennen et al. |
| 2004/0015337 A1 | 1/2004 | Thomas et al. |
| 2004/0018500 A1 | 1/2004 | Glassbrook et al. |
| 2004/0019598 A1 | 1/2004 | Huang et al. |
| 2004/0019688 A1 | 1/2004 | Nickerson et al. |
| 2004/0024534 A1 | 2/2004 | Hsu |
| 2004/0034652 A1 | 2/2004 | Hofmann et al. |
| 2004/0093331 A1 | 5/2004 | Garner et al. |
| 2004/0093334 A1 | 5/2004 | Scherer |
| 2004/0111410 A1 | 6/2004 | Burgoon et al. |
| 2004/0122705 A1 | 6/2004 | Sabol et al. |
| 2004/0158581 A1 | 8/2004 | Kotlyar et al. |
| 2004/0172287 A1 | 9/2004 | O'Toole et al. |
| 2004/0172313 A1 | 9/2004 | Stein et al. |
| 2004/0175700 A1 | 9/2004 | Geesaman |
| 2004/0177071 A1 | 9/2004 | Massey et al. |
| 2004/0193019 A1 | 9/2004 | Wei |
| 2004/0197799 A1 | 10/2004 | Williamson et al. |
| 2004/0219493 A1 | 11/2004 | Phillips |
| 2004/0221855 A1 | 11/2004 | Ashton |
| 2004/0242454 A1 | 12/2004 | Gallant |
| 2004/0243443 A1 | 12/2004 | Asano et al. |
| 2004/0243545 A1 | 12/2004 | Boone et al. |
| 2004/0254920 A1 | 12/2004 | Brill et al. |
| 2005/0021240 A1 | 1/2005 | Berlin et al. |
| 2005/0026117 A1 | 2/2005 | Judson et al. |
| 2005/0026119 A1 | 2/2005 | Ellis et al. |
| 2005/0032066 A1 | 2/2005 | Heng et al. |
| 2005/0037405 A1 | 2/2005 | Caspi et al. |
| 2005/0055365 A1 | 3/2005 | Ramakrishnan et al. |
| 2005/0064476 A1 | 3/2005 | Huang et al. |
| 2005/0090718 A1 | 4/2005 | Dodds |
| 2005/0112684 A1 | 5/2005 | Holzle |
| 2005/0120019 A1 | 6/2005 | Rigoutsos et al. |
| 2005/0143928 A1 | 6/2005 | Moser et al. |
| 2005/0154627 A1 | 7/2005 | Zuzek et al. |
| 2005/0158788 A1 | 7/2005 | Schork et al. |
| 2005/0164704 A1 | 7/2005 | Winsor |
| 2005/0170321 A1 | 8/2005 | Scully |
| 2005/0170528 A1 | 8/2005 | West et al. |
| 2005/0176057 A1 | 8/2005 | Bremer et al. |
| 2005/0181516 A1 | 8/2005 | Dressman et al. |
| 2005/0191678 A1 | 9/2005 | Lapointe et al. |
| 2005/0191731 A1 | 9/2005 | Judson et al. |
| 2005/0203900 A1 | 9/2005 | Nakamura et al. |
| 2005/0208454 A1 | 9/2005 | Hall |
| 2005/0216208 A1 | 9/2005 | Saito et al. |
| 2005/0228595 A1* | 10/2005 | Cooke | G06F 7/02 702/20 |
| 2005/0256649 A1 | 11/2005 | Roses |
| 2005/0260610 A1 | 11/2005 | Kurtz et al. |

(56) References Cited

U.S. PATENT DOCUMENTS

| | | |
|---|---|---|
| 2005/0278125 A1 | 12/2005 | Harwood et al. |
| 2006/0020398 A1 | 1/2006 | Vernon et al. |
| 2006/0020614 A1 | 1/2006 | Kolawa et al. |
| 2006/0025929 A1 | 2/2006 | Eglington |
| 2006/0052945 A1 | 3/2006 | Rabinowitz et al. |
| 2006/0059159 A1 | 3/2006 | Truong et al. |
| 2006/0064415 A1 | 3/2006 | Guyon et al. |
| 2006/0129034 A1 | 6/2006 | Kasabov et al. |
| 2006/0136143 A1 | 6/2006 | Avinash et al. |
| 2006/0195335 A1 | 8/2006 | Christian et al. |
| 2006/0200319 A1 | 9/2006 | Brown |
| 2006/0218111 A1 | 9/2006 | Cohen |
| 2006/0235881 A1 | 10/2006 | Masarie et al. |
| 2006/0257888 A1 | 11/2006 | Zabeau et al. |
| 2006/0293921 A1 | 12/2006 | McCarthy et al. |
| 2007/0011173 A1 | 1/2007 | Agostino |
| 2007/0016568 A1 | 1/2007 | Amir et al. |
| 2007/0027850 A1 | 2/2007 | Chan et al. |
| 2007/0027917 A1 | 2/2007 | Ariel et al. |
| 2007/0037182 A1 | 2/2007 | Gaskin et al. |
| 2007/0050354 A1 | 3/2007 | Rosenberg |
| 2007/0061085 A1 | 3/2007 | Fernandez |
| 2007/0061166 A1 | 3/2007 | Ramasubramanian et al. |
| 2007/0061197 A1 | 3/2007 | Ramer et al. |
| 2007/0061424 A1 | 3/2007 | Mattaway |
| 2007/0078680 A1 | 4/2007 | Wennberg |
| 2007/0106536 A1 | 5/2007 | Moore |
| 2007/0106754 A1 | 5/2007 | Moore |
| 2007/0111247 A1 | 5/2007 | Stephens et al. |
| 2007/0116036 A1 | 5/2007 | Moore |
| 2007/0122824 A1 | 5/2007 | Tucker et al. |
| 2007/0220017 A1 | 9/2007 | Zuzarte et al. |
| 2007/0239554 A1 | 10/2007 | Lin et al. |
| 2007/0271292 A1 | 11/2007 | Acharya et al. |
| 2007/0294113 A1 | 12/2007 | Settimi |
| 2008/0040046 A1 | 2/2008 | Chakraborty et al. |
| 2008/0040151 A1 | 2/2008 | Moore |
| 2008/0081331 A1 | 4/2008 | Myres et al. |
| 2008/0082955 A1 | 4/2008 | Andreessen et al. |
| 2008/0108881 A1 | 5/2008 | Stupp et al. |
| 2008/0114737 A1 | 5/2008 | Neely et al. |
| 2008/0131887 A1 | 6/2008 | Stephan et al. |
| 2008/0154566 A1 | 6/2008 | Myres et al. |
| 2008/0162510 A1 | 7/2008 | Baio et al. |
| 2008/0189047 A1 | 8/2008 | Wong et al. |
| 2008/0227063 A1 | 9/2008 | Kenedy et al. |
| 2008/0228043 A1 | 9/2008 | Kenedy et al. |
| 2008/0228410 A1 | 9/2008 | Kenedy et al. |
| 2008/0228451 A1 | 9/2008 | Kenedy et al. |
| 2008/0228677 A1 | 9/2008 | Kenedy et al. |
| 2008/0228698 A1 | 9/2008 | Kenedy et al. |
| 2008/0228699 A1 | 9/2008 | Kenedy et al. |
| 2008/0228700 A1 | 9/2008 | Kenedy et al. |
| 2008/0228701 A1 | 9/2008 | Kenedy et al. |
| 2008/0228702 A1 | 9/2008 | Kenedy et al. |
| 2008/0228704 A1 | 9/2008 | Kenedy et al. |
| 2008/0228705 A1 | 9/2008 | Kenedy et al. |
| 2008/0228706 A1 | 9/2008 | Kenedy et al. |
| 2008/0228708 A1 | 9/2008 | Kenedy et al. |
| 2008/0228722 A1 | 9/2008 | Kenedy et al. |
| 2008/0228753 A1 | 9/2008 | Kenedy et al. |
| 2008/0228756 A1 | 9/2008 | Kenedy et al. |
| 2008/0228757 A1 | 9/2008 | Kenedy et al. |
| 2008/0228765 A1 | 9/2008 | Kenedy et al. |
| 2008/0228766 A1 | 9/2008 | Kenedy et al. |
| 2008/0228767 A1 | 9/2008 | Kenedy et al. |
| 2008/0228768 A1 | 9/2008 | Kenedy et al. |
| 2008/0228797 A1 | 9/2008 | Kenedy et al. |
| 2008/0243843 A1 | 10/2008 | Kenedy et al. |
| 2008/0256023 A1 | 10/2008 | Nair |
| 2008/0300958 A1 | 12/2008 | Gluck |
| 2009/0012928 A1 | 1/2009 | Lussier et al. |
| 2009/0043752 A1 | 2/2009 | Kenedy et al. |
| 2009/0083654 A1 | 3/2009 | Nickerson et al. |
| 2009/0099789 A1 | 4/2009 | Stephan et al. |
| 2009/0112871 A1 | 4/2009 | Hawthorne et al. |
| 2009/0118131 A1 | 5/2009 | Avey et al. |
| 2009/0119083 A1 | 5/2009 | Avey et al. |
| 2009/0222517 A1 | 9/2009 | Kalofonos et al. |
| 2009/0271375 A1 | 10/2009 | Hyde et al. |
| 2009/0319610 A1 | 12/2009 | Nikolayev et al. |
| 2009/0326832 A1 | 12/2009 | Heckerman et al. |
| 2010/0041958 A1 | 2/2010 | Leuthardt et al. |
| 2010/0042438 A1 | 2/2010 | Moore et al. |
| 2010/0063830 A1 | 3/2010 | Kenedy et al. |
| 2010/0063835 A1 | 3/2010 | Kenedy et al. |
| 2010/0063865 A1 | 3/2010 | Kenedy et al. |
| 2010/0063930 A1 | 3/2010 | Kenedy et al. |
| 2010/0070292 A1 | 3/2010 | Kenedy et al. |
| 2010/0070455 A1 | 3/2010 | Halperin et al. |
| 2010/0076950 A1 | 3/2010 | Kenedy et al. |
| 2010/0076988 A1 | 3/2010 | Kenedy et al. |
| 2010/0169262 A1 | 7/2010 | Kenedy et al. |
| 2010/0169313 A1 | 7/2010 | Kenedy et al. |
| 2010/0169338 A1 | 7/2010 | Kenedy et al. |
| 2010/0223281 A1 | 9/2010 | Hon et al. |
| 2011/0004628 A1 | 1/2011 | Armstrong et al. |
| 2011/0078168 A1 | 3/2011 | Kenedy et al. |
| 2011/0184656 A1 | 7/2011 | Kenedy et al. |
| 2011/0196872 A1 | 8/2011 | Sims et al. |
| 2012/0270190 A1 | 10/2012 | Kenedy et al. |
| 2012/0270794 A1 | 10/2012 | Eriksson et al. |
| 2013/0013217 A1 | 1/2013 | Stephan et al. |
| 2013/0345988 A1 | 12/2013 | Avey et al. |
| 2014/0006433 A1 | 1/2014 | Hon et al. |
| 2014/0067355 A1 | 3/2014 | Noto et al. |
| 2014/0098344 A1 | 4/2014 | Gierhart et al. |
| 2015/0100243 A1 | 4/2015 | Myres et al. |
| 2015/0227610 A1 | 8/2015 | Chowdry et al. |
| 2015/0248473 A1 | 9/2015 | Kenedy et al. |
| 2015/0288780 A1 | 10/2015 | El Daher |
| 2015/0347566 A1 | 12/2015 | Kenedy et al. |
| 2016/0026755 A1 | 1/2016 | Byrnes et al. |
| 2016/0091499 A1 | 3/2016 | Sterling et al. |
| 2016/0103950 A1 | 4/2016 | Myres et al. |
| 2016/0171155 A1 | 6/2016 | Do et al. |
| 2016/0277408 A1 | 9/2016 | Hawthorne et al. |
| 2016/0350479 A1 | 12/2016 | Han et al. |
| 2017/0011042 A1 | 1/2017 | Kermany et al. |
| 2017/0017752 A1 | 1/2017 | Noto et al. |
| 2017/0053089 A1 | 2/2017 | Kenedy et al. |
| 2017/0185719 A1 | 6/2017 | Kenedy et al. |
| 2017/0220738 A1 | 8/2017 | Barber et al. |
| 2017/0228498 A1 | 8/2017 | Hon et al. |
| 2017/0277827 A1 | 9/2017 | Granka et al. |
| 2017/0277828 A1 | 9/2017 | Avey et al. |
| 2017/0329866 A1 | 11/2017 | Macpherson |
| 2017/0329891 A1 | 11/2017 | Macpherson et al. |
| 2017/0329899 A1 | 11/2017 | Bryc et al. |
| 2017/0329901 A1 | 11/2017 | Chowdry et al. |
| 2017/0329902 A1 | 11/2017 | Bryc et al. |
| 2017/0329904 A1 | 11/2017 | Naughton et al. |
| 2017/0329915 A1 | 11/2017 | Kittredge et al. |
| 2017/0329924 A1 | 11/2017 | Macpherson et al. |
| 2017/0330358 A1 | 11/2017 | Macpherson et al. |
| 2018/0181710 A1 | 6/2018 | Avey et al. |
| 2018/0307778 A1 | 10/2018 | Macpherson |
| 2019/0012431 A1* | 1/2019 | Hon ................... G06F 16/9535 |
| 2019/0034163 A1 | 1/2019 | Kenedy et al. |
| 2019/0114219 A1 | 4/2019 | Do et al. |
| 2019/0139623 A1 | 5/2019 | Bryc et al. |
| 2019/0206514 A1* | 7/2019 | Avey ................... G16B 45/00 |
| 2019/0267115 A1 | 8/2019 | Avey et al. |
| 2019/0281061 A1 | 9/2019 | Hawthorne et al. |
| 2019/0384777 A1 | 12/2019 | Naughton et al. |
| 2020/0137063 A1 | 4/2020 | Hawthorne et al. |
| 2020/0210143 A1 | 7/2020 | Kenedy et al. |
| 2020/0372974 A1 | 11/2020 | Chowdry et al. |
| 2021/0020266 A1 | 1/2021 | Freyman et al. |
| 2021/0043278 A1* | 2/2021 | Hon ................... G06N 5/048 |
| 2021/0043279 A1 | 2/2021 | Hon et al. |
| 2021/0043280 A1* | 2/2021 | Hon ................... G06F 16/9535 |
| 2021/0043281 A1 | 2/2021 | Macpherson et al. |
| 2021/0058398 A1 | 2/2021 | Hawthorne et al. |

(56) References Cited

U.S. PATENT DOCUMENTS

| | | | |
|---|---|---|---|
| 2021/0074385 A1* | 3/2021 | Hon | G06N 5/048 |
| 2021/0166452 A1 | 6/2021 | Jewett et al. | |
| 2021/0166823 A1 | 6/2021 | Kenedy et al. | |
| 2021/0193257 A1 | 6/2021 | Freyman et al. | |
| 2021/0209134 A1 | 7/2021 | Kenedy et al. | |
| 2021/0225458 A1 | 7/2021 | Hon et al. | |
| 2021/0233665 A1 | 7/2021 | Kenedy et al. | |
| 2021/0250357 A1 | 8/2021 | Hawthorne et al. | |
| 2021/0313013 A1 | 10/2021 | Hon et al. | |
| 2021/0375392 A1 | 12/2021 | Polcari et al. | |
| 2022/0044761 A1 | 2/2022 | O'Connell et al. | |
| 2022/0051751 A1 | 2/2022 | Wilton et al. | |
| 2022/0103560 A1 | 3/2022 | Hawthorne et al. | |
| 2022/0115139 A1 | 4/2022 | Paradarami et al. | |
| 2022/0139501 A1 | 5/2022 | Hon et al. | |
| 2022/0157405 A1 | 5/2022 | Avey et al. | |
| 2022/0198726 A1 | 6/2022 | Jewett et al. | |

FOREIGN PATENT DOCUMENTS

| | | |
|---|---|---|
| WO | WO-0222165 A1 | 3/2002 |
| WO | WO-02080079 A2 | 10/2002 |
| WO | WO-03060652 A2 | 7/2003 |
| WO | WO-03076895 A2 | 9/2003 |
| WO | WO 2004/029298 A2 | 4/2004 |
| WO | WO-2004031912 A2 | 4/2004 |
| WO | WO-2004048551 A2 | 6/2004 |
| WO | WO-2004051548 A2 | 6/2004 |
| WO | WO-2004075010 A2 | 9/2004 |
| WO | WO-2004097577 A2 | 11/2004 |
| WO | WO-2005086891 A2 | 9/2005 |
| WO | WO-2005109238 A2 | 11/2005 |
| WO | WO-2006052952 A2 | 5/2006 |
| WO | WO 2006/089238 A3 | 8/2006 |
| WO | WO-2006084195 A2 | 8/2006 |
| WO | WO-2007061881 A2 | 5/2007 |
| WO | WO 2008/042232 A2 | 4/2008 |
| WO | WO 2016/073953 | 5/2016 |
| WO | WO-2021243094 A1 | 12/2021 |
| WO | WO-2022036178 A1 | 2/2022 |
| WO | WO-2022076909 A1 | 4/2022 |

OTHER PUBLICATIONS

"parallel computing" Wikipedia.com downloaded Apr. 14, 2021 (Year: 2021).*
"bit-level parallelism" definition Wikipedia.com downloaded Apr. 14, 2021 (Year: 2021).*
"parallel processing definition" Techopedia.com downloaded Apr. 14, 2021 (Year: 2021).*
Parallel processing definition Encyclopedia.com downloaded Apr. 14, 2021 (Year: 2021).*
Garrett, Paul: The mathematics of coding: Information, compression, error correction and finite fields. University of Minnesota. Downloaded Apr. 13, 2021 (Year: 2021).*
Keprt et al. Binary factor analysis with help of formal concepts. In Snasel et al (eds) CLA 2004, p. 90-101. ISBN 80-248-0597-9 (Year: 2004).*
Office Action dated May 31, 2012 in U.S. Appl. No. 12/644,791.
Final Office Action dated Dec. 7, 2012 in U.S. Appl. No. 12/644,791.
Notice of Allowance dated Feb. 25, 2013 in U.S. Appl. No. 12/644,791.
Office Action dated Feb. 18, 2016 in U.S. Appl. No. 13/871,744.
Office Action dated Mar. 14, 2016 in U.S. Appl. No. 13/871,744.
Office Action dated May 18, 2018 in U.S. Appl. No. 15/264,493.
Office Action dated Mar. 3, 2020 in U.S. Appl. No. 15/664,619.
Notice of Allowance dated Aug. 19, 2020 in U.S. Appl. No. 15/664,619.
International Search Report and Written Opinion dated Mar. 3, 2010 in PCT/US2009/06706.
International Preliminary Report on Patentability dated Jul. 5, 2011 in PCT/US2009/06706.
International Preliminary Report on Patentability dated Apr. 7, 2009 in PCT Application No. PCT/US2007/020884.
Written Opinion dated Apr. 8, 2008 in PCT Application No. PCT/US2007/020884.
International Search Report dated Apr. 8, 2008 in PCT Application No. PCT/US2007/020884.
Extended European Search Report dated Oct. 25, 2016 in EP 09836517.4.
International Preliminary Report on Patentability dated Jul. 14, 2011 in PCT/US2009/006706.
Extended European Search Report dated Oct. 9, 2017 in Application No. 17172048.5.
Abecasis, et al., "Extent and distribution of linkage disequilibrium in three genomic regions" Am. J. Hum. Genet. 68, (2001) pp. 191-197.
Abecasis, et al., "GOLD—Graphical overview of linkage disequilibrium" Bioinformatics, vol. 16, No. 2, (2000) pp. 182-183.
Abecasis, et al., "GRR: graphical representation of relationship errors" Bioinformatics 17, (2001) pp. 742-743.
Abecasis, et al., "Handling marker-marker linkage disequilibrium: pedigree analysis with clustered markers" Am. J. Hum. Genet. 77 (2005) pp. 754-767.
Abecasis, et al., "Linkage disequilibrium: ancient history drives the new genetics" Hum. Hered. 59, (2005) pp. 118-124.
Abecasis, et al., "MaCH: Using sequence and genotype data to estimate haplotypes and unobserved genotypes" Genetic Epidemiology 34 (2010) pp. 816-834.
Abecasis, et al., "Merlin-rapid analysis of dense genetic maps using sparse gene flow trees" Nat. Genet. 2002, 30 (2002) pp. 97-101.
Abney, et al., "Quantitative-Trait Homozygosity and Association Mapping and Empirical Genomewide Significance in Large, Complex Pedigrees: Fasting Serum-Insulin Level in the Hutterites" Am. J. Hum. Genet. 70, (2002) pp. 920-934.
Albers, et al., "Multipoint Approximations of Identity-by-descent probabilities for accurate linkage analysis of distantly related individuals," The American Journal of Human Genetics 82, Mar. 2008, pp. 607-622.
Alexander, et al., "Fast model-based estimation of ancestry in unrelated individuals" Genome Research 19, (2009) pp. 1655-1664.
Almasy, et al. "Multipoint quantitative-trait linkage analysis in general pedigrees" Am. J. Hum. Genet. 62: (1998) pp. 1198-1211.
Almudevar, A., "A Bootstrap Assessment of Variability in Pedigree Reconstruction Based on DNA Markers" Biometrics, vol. 57, Sep. 2001, pp. 757-763.
Almudevar, A., "A simulated annealing algorithm for maximum likelihood pedigree reconstruction" Theoretical Population Biology, vol. 63, (2003) pp. 63-75.
Almudevar, et al., "Estimation of single-generation sibling relationship based on DNA markers" Journal Agricultural Biological, and Environmental Statistics, vol. 4, No. 2, (1999) pp. 136-165.
Almudevar, et al., "Most powerful permutation invariant tests for relatedness hypotheses based on genotypic data" Biometrics 57, Dec. 2001, pp. 1080-1088.
Altschul, et al. "Basic Local Alignment Search Tool" J. Mol. Biol. (1990) 215, pp. 403-410.
Amorim, et al., "Pros and cons in the use of SNP's in forensic kinship investigation: a comparative analysis with STRs" Forensic Sci. Int. 150, (2005) pp. 17-21.
Amos and Elston, "Robust Methods for the Detection of Genetic Linkage for Quantitative Data From Pedigree" Genetic Epidemiology 6, (1989) pp. 349-360.
Amos, et al., "The Probabilistic Determination of Identity-by-Descent Sharing for Pairs of Relatives from Pedigrees" Am. J. Hum. Genet. 47 (1990) pp. 842-853.
Ayers, et al. "Reconstructing Ancestral Haplotypes with a Dictionary Model" Department of Statistics Papers, Department of Statistics, UCLA, UC Los Angeles, Mar. 28, 2005, pp. 1-41.
Bacolod, et al., "The Signatures of Autozygosity among Patients with Colorectal Cancer" Cancer Res. vol. 68, No. 8, Apr. 15, 2008, pp. 2610-2621.
Balding, et al., "A method for quantifying differentiation between populations at multi-allelic loci and its implications for investigating identity and paternity" Genetica, 96 (1995) pp. 3-12.

(56) References Cited

OTHER PUBLICATIONS

Ballantyne, J., "Mass disaster genetics" Nature Genet. 15, (1997) pp. 329-331.

Belkhir, et al., "IDENTIX, a software to test for relatedness in a population using permutation methods" Molecular Ecology, 2, (2002) pp. 611-614.

Bieber, et al., "Finding criminals through DNA of their relatives" Science 312, (2006) pp. 1315-1316.

Blackwell et al., "Identity by Descent Genome Segmentation Based on Single Nucleotide Polymorphism Distributions," American Association for Artificial Intelligence, 1999, pp. 54-59.

Blouin, M.S. et al., "Use of microsatellite loci to classify individuals by relatedness" Molecular Ecology, vol. 5, (1996) pp. 393-401.

Blouin, M.S., "DNA-based methods for pedigree reconstruction and kinship analysis in natural populations" Trends in Ecology and Evolution, vol. 18, No. 10, Oct. 2003, pp. 503-511.

Boehnke, et al., "Accurate Inference of Relationships in Sib-Pair Linkage Studies" Am. J. Hum. Genet. 61, (1997) pp. 423-429.

Boehnke, M., "Allele frequency estimation from data on relatives" Am. J. Hum. Genet. 48, (1991) pp. 22-25.

Brenner, C.H. "Kinship Analysis by DNA When There Are Many Possibilities" Progress in Forensic Genetics, vol. 8, (2000) pp. 94-96, Elsevier Science.

Brenner, C.H., "Issues and strategies in the DNA identification of World Trade Center victims" Theor. Popul. Biol. 63, (2003) pp. 173-178.

Brenner, C.H., "Symbolic kinship program" Genetics, 145, (1997) pp. 535-542.

Brief For Defendants—Appellees Ancestry.com DNA, LLC, Ancestry. com Operations Inc., And Ancestry.com LLC, Case No. 2019-1222, Document: 24, Filed on Mar. 18, 2019, in The US Court of Appeals For The Federal Circuit, pp. 1-76.

Brief of Appellant 23AndMe, Inc., Case No. 2019-1222, Document 19, Filed on Feb. 4, 2019, in The US Court of Appeals for the Federal Circuit, pp. 1-140.

Broman, et al., "Estimation of pairwise relationships in the presence of genotyping errors" Am. J. Hum. Genet. 63, (1998) pp. 1563-1564.

Broman, et al., "Long Homozygous Chromosomal Segments in Reference Families from the Centre d'Etude du Polymorphisme Humain" Am. J. Hum. Genet. 65, (1999) pp. 1493-1500.

Browning, et al., "A unified approach to Genotype imputation and Haplotype-Phase inference for large data sets of Trios and unrelated individuals" Am. J. Hum. Genet. 84, (2009) pp. 210-223.

Browning, et al., "Efficient Multilocus Association Testing for Whole Genome Association Studies Using Localized Haplotype Clustering" Genetic Epidemiology, vol. 31, 2007 pp. 365-375.

Browning, et al., "On reducing the statespace of hidden markov models for the identity by descent process" Theor. Popul. Biol. 62, (2002) pp. 1-8.

Browning, et al., "Rapid and Accurate Haplotype Phasing and Missing-Data Inference for Whole-Genome Association Studies By Use of Localized Haplotype Clustering," The American Journal of Human Genetics, vol. 81, Nov. 2007, pp. 1084-1097.

Browning, et al., "Identity by Descent Between Distant Relatives: Detection and Applications." Annual Review of Genetics, vol. 46, Dec. 2012, pp. 617-633.

Browning, S. et al., "Estimation of pairwise identity by descent from dense genetic marker data in a population sample of haplotypes," Genetics, vol. 178, No. 4, Apr. 22, 2008, pp. 2123-2132. <doi: 10.1534/genetics.107.084624>.

Cannings, C., "The identity by descent process along the chromosome" Human Heredity, 56 (2003) pp. 126-130.

Carlson, et al., "Mapping complex disease loci in whole-genome association studies" Nature 429 (2004) pp. 446-452.

Cavalli-Sforza, L., "The Human Genome Diversity Project: past, present and future," Nature Reviews, Genetics, vol. 6, Apr. 2005, pp. 333-340.

Chapman, et al., "The effect of population history on the lengths of ancestral chromosome segments" Genetics, 162, Sep. 2002, pp. 449-458.

Chen et al., "Family-Based Association Test for Genomewide Association Scans," The American Journal of Human Genetics, vol. 81, Nov. 2007, pp. 913-926.

Chen, et al., "Robust relationship inference in genome-wide association studies" Bioinformatics 26 No. 22, 2010, pp. 2867-2873.

Cheung, et al., "Linkage-disequilibrium mapping without genotyping" Nature Genetics 18, (1998) pp. 225-230.

Choi, et al., "Case-control association testing in the presence of unknown relationships" Genet. Epidem. 33, (2009) pp. 668-678.

Cockerman, C., "Higher order probability functions of identity of alleles by descent" Genetics 69, (1971) pp. 235-246.

Complaint filed In the United States District Court in and for the Northern District of California, captioned *23andMe, Inc.* v. *Ancestry. com DNA, LLC, Ancestry.com Operations Inc., and Ancestry.com LLC*, filed on May 11, 2018, assigned Case No. 18-cv-02791-JCS, for "Complaint for Patent Infringement, Violations of the Lanham Act, Cal. Bus. & Prof. Code §§ 17200 And 17500, and Declaratory Relief of No Trademark Infringement and Trademark Invalidity."

Cordell, et al., "Two-locus maximum Lod score analysis of a multifactorial trait: joint consideration of IDDM2 and IDDM4 with IDDM1 in Type 1 diabetes" Am. J. Hum. Genet. 57, (1995) pp. 920-934.

Cowell, R.G., "FINEX: A probabilistic expert system for forensic identification" Forensic Science International, 134, (2003) pp. 196-206.

Crawford, et al., "Evidence for substantial fine-scale variation in recombination rates across the human genome," Nature Genetics, vol. 36, No. 7, Jul. 2004, pp. 700-706.

Cudworth, et al., "Evidence for HL-A-linked genes in "juvenile" diabetes mellitus" Br. Med. J. 3, (1975) pp. 133-135.

Curtis, et al., "Using risk calculation to implement an extended relative pair analysis" Ann. Hum. Genet. 58 (1994) pp. 151-162.

Defendants' Notice of Motion And Motion To Dismiss Plaintiff's Complaint, filed in the United States District Court in and for the Northern District of California LLC on Jun. 29, 2018, Case No. 18-cv-02791-JCS, Re *23andMe, Inc.* v. *Ancestry.com DNA, LLC, Ancestry.com Operations Inc., and Ancestry.com*.

Delaneau, et al., "A Linear complexity phasing method for thousands of genomes," Nature Methods, vol. 9, No. 2, Feb. 2012, pp. 179-184.

Denniston, C., "Probability and genetic relationship" Ann. Hum. Genet., Lond. (1975), 39, pp. 89-103.

Di Rienzo, et al., "An evolutionary framework for common diseases: the ancestral-susceptibility model" Trends Genet. 21 (2005) pp. 596-601.

Dodds, et al. "Using genetic markers in unpedigreed populations to detect a heritable trait" J. Zhejiang Univ. Sci. 2007 8(11):782-786.

Donnelly, K.P., "The probability that related individuals share some section of genome identical by descent" Theor. Popul. Biol. 23 (1983) pp. 34-63.

Douglas, et al., "A multipoint method for detecting genotyping errors and mutations in sibling-pair linkage data" Am. J. Hum. Genet. 66 (2000) pp. 1287-1297.

Duffy, et al. "An integrated genetic map for linkage analysis" Behav. Genet. 36, 2006, pp. 4-6.

Dupuis, et al., "Statistical methods for linkage analysis of complex traits from high resolution maps of identity by descent" Genetics 140 (1995) pp. 843-856.

Eding, et al., "Marker-based estimates of between and within population kinships for the conservation of genetic diversity" J. Anim. Breed. Genet. 118 (2001), pp. 141-159.

Ehm, et al., "A test statistic to detect errors in sib-pair relationships" Am. J. Hum. Genet. 62 (1998) pp. 181-188.

Elston, et al., "A general model for the genetic analysis of pedigree data" Hum. Hered. 21, (1971) pp. 523-542.

Epstein, et al., "Improved inference of relationship for pairs of individuals" Am. J. Hum. Genet., vol. 67, (2000) pp. 1219-1231.

Falush, et al., "Inference of population structure using multilocus genotype data:linked loci and correlated allele frequencies" Genetics 164, (2003) pp. 1567-1587.

(56) References Cited

OTHER PUBLICATIONS

Feingold, E. "Markov processes for modeling and analyzing a new genetic mapping method" J. Appl. Prob. 30 (1993) pp. 766-779.
Feingold, et al., "Gaussian Models for Genetic Linkage Analysis Using Complete High-Resolution Maps of Identity by Descent," Am. J. Hum. Genet. 53 (1993) pp. 234-251.
Fisher, RA "A Fuller Theory of 'Junctions' in Inbreeding" Heredity, 8 (1954) pp. 187-197.
Fisher, RA "The theory of inbreeding" Department of Genetics, Cambridge University, Eng. Edinburgh, London, Oliver & Boyd, Ltd., (1949) pp. 97-100.
Frazer, et al., "A second generation human haplotype map of over 3.1 million SNPs" vol. 449, Oct. 18, 2007, pp. 851-861. <doi:10.1038/nature06258>.
Fuchsberger, et al., "Minimac2: faster genotype imputation," Bioinformatics, vol. 31, No. 5, Oct. 22, 2014, pp. 782-784. <doi:10.1093/bioinformatics/btu704>.
Gaytmenn, et al., "Determination of the sensitivity and specificity of sibhip calculations using AmpF/STR Profiler Plus" Int. J. Legal Med. 116, (2002) pp. 161-164.
George, et al., "Discovering disease genes: Multipoint linkage analyses via a new Markov Chain Monte Carlo approach" Statistical Science, vol. 18, No. 4, (2003) pp. 515-535.
Gillanders, et al., "The Value of Molecular Haplotypes in a Family-Based Linkage Study" Am. J. Hum. Genet. 79 (2006) pp. 458-468.
Glaubitz, et al., "Prospects for inferring pairwise relationships with single nucleotide polymorphisms" Molecular Ecology, 12 (2003) pp. 1039-1047.
Goodnight, et al., "Computer software for performing likelihood tests of pedigree relationship using genetic markers" Molecular Ecology, vol. 8, (1999) pp. 1231-1234.
Grafen, A., "A geometric view of relatedness" Oxford Surveys in Evolutionary Biology, 2 (1985) pp. 39-89.
Grant, et al., "Significance testing for direct identity-by-descent mapping" Ann. Hum. Genet. 63, (1999) pp. 441-454.
Greenspan, et al., "Model-based inference of haplotype block variation" J. Comput. Biol. 11, (2004) pp. 493-504.
Griffiths, et al., "Ancestral inference of samples of DNA sequences with recombination" Journal of Computational Biology, vol. 3, No. 4 (1996) pp. 479-502.
Gudbjartsson, et al., "Allegro, a new computer program for multipoint linkage analysis" Nat. Genet. 25, (2000) pp. 12-13.
Guo, S., "Proportion of Genome Shared Identical by Descent by Relatives: Concept, Computation, and Applications" Am. J. Hum. Genet. 56 (1995) pp. 1468-1476.
Gusev, et al., "Whole population, genome-wide mapping of hidden relatedness," Genome Research, vol. 19, 2009, pp. 318-326.
Hajnal, J., "Concepts of random mating and the frequency of consanguineous marriages," Proceedings of the Royal Society of London. Series B. Biological Sciences 159, No. 974 (1963) pp. 125-177.
Hardy, O.J., "Estimation of pairwise relatedness between individuals and characterization of isolation-by-distance processes using dominant genetic markers" Molecular Ecology, 12 (2003) pp. 1577-1588.
Harris, D.L., "Genotypic covariances between inbred relatives" Genetics 50, (1964) pp. 1319-1348.
Hayward, et al., "Fibrillin-1 mutations in Marfan syndrome and other type-1 fibrillinopathies" Hum. Mutat. 10 (1997) pp. 415-423.
Heath, et al., "A novel approach to search for identity by descent in small samples of patients and controls from the same Mendelian breeding unit: a pilot study in myopia" Human Heredity, vol. 52, Feb. 2001, pp. 183-190.
Henn, B.M., et al. "Cryptic Distant Relatives Are Common in Both Isolated and Cosmopolitan Genetic Samples," PLosOne, vol. 7, No. 4, Apr. 3, 2012, pp. 1-3. <doi:10.1371/journal.pone.0034267>.
Hepler, A.B., "Improving forensic identification using Bayesian Networks and Relatedness Estimation" Ph.D Thesis, NCSU, Raleigh (2005) pp. 1-131.
Hernández-Sánchez, et al., "On the prediction of simultaneous inbreeding coefficients at multiple loci" Genet. Res. 83 (2004) pp. 113-120.
Hernández-Sánchez, et al., "Prediction of IBD based on population history for fine gene mapping" Genet. Sel. Evol. 38 (2006) pp. 231-252.
Heyer, et al., "Variability of the genetic contribution of Quebec population founders associated to some deleterious genes" Am. J. Hum. Genet. 56 (1995) pp. 970-978.
Hill, et al. "Prediction of multilocus identity-by-descent" Genetics 176, Aug. 2007, pp. 2307-2315.
Hill, et al., "Linkage disequilibrium in finite populations" Theor. Appl. Genet. 38, (1968) pp. 226-231.
Hill, et al., "Prediction of multi-locus inbreeding coefficients and relation to linkage disequilibrium in random mating populations" Theor Popul Biol. Sep. 2007, 72(2), pp. 179-185. <doi:10.1016/j.tpb.2006.05.006>.
Hill, et al., "Variances and covariances of squared linkage disequilibria in finite populations" Theor. Pop. Biol., 33 (1988) pp. 54-78, [PubMed: 3376052].
Hill, W.G., "Disequilibrium among several linked neutral genes in finite population. II Variances and covariances of disequilibria" Theor. Pop. Biol., vol. 6, 1974, pp. 184-198.
Hinrichs, et al., "Multipoint identity-by-descent computations for single-point polymorphism and microsatellite maps," BMC Genet. 6, Dec. 30, 2005, S34. <doi:10.1186/1471-2156-6-S1-S34>.
Houwen, et al., "Genomic screening by searching for shared segments: mapping a gene for benign recurrent intrahepatic cholestasis" Nature Genetics vol. 8, Dec. 1994, pp. 380-386.
Howie, et al., "A Flexible and Accurate Genotype Imputation Method for the Next Generation of Genome-Wide Association Studies," PLoS Genetics, vol. 5, No. 6, Jun. 2009, pp. 1-15.
Howie, et al., "Fast and accurate genotype imputation in genome-wide association studies through pre-phasing," Nature Genetics, vol. 44, No. 8, Aug. 2012, pp. 955-960.
Hu, X.S., "Estimating the correlation of pairwise relatedness along chromosomes" Heredity 94, (2004) pp. 338-346, [PubMed: 15354191].
Huang, et al. "Whole genome DNA copy number changes identified by high density oligonucleotide arrays," Hum. Genomics vol. 1, No. 4, May 2004, pp. 287-299.
Huang, et al., "Ignoring linkage disequilibrium among tightly linked markers induces false-positive evidence of linkage for affected sib pair analysis" Am. J. Hum. Genet. 75, (2004) pp. 1106-1112.
Idury, et al., "A faster and more general hidden Markov model algorithm for multipoint likelihood calculations" Hum. Hered. 47(1997) pp. 197-202.
Jacquard, A., "Genetic information given by a relative" Biometrics, 28, (1972) pp. 1101-1114.
Jones, et al., "Methods of parentage analysis in natural populations" Molecular Ecology 12 (2003) pp. 2511-2523.
Karigl, G., "A recursive algorithm for the calculation of identity coefficients" Ann. Hum. Genet. 45, (1981) pp. 299-305.
Keith, J.M., et al., "Calculation of IBD Probabilities with Dense SNP or Sequence Data" Genetic Epidemiology 32 (2008) pp. 513-519.
Kent, J.W. "BLAT—The BLAST-Like Alignment Tool" Genome Res. 2002, vol. 12, pp. 656-664.
Kimmel, et al., "A block-free hidden Markov model for genotypes and its application to disease association" J. Comput. Biol. 12, (2005a) pp. 1243-1260.
Kimmel, et al., "GERBIL: genotype resolution and block identification using likelihood" Proc. Natl. Acad. Sci. USA 102, (2005b) pp. 158-162.
Kong, A. et al., "Detection of sharing by descent, long-range phasing and haplotype imputation," Nature Genetics, vol. 40, No. 9, Sep. 2008, pp. 1068-1075.
Kong, et al., "A combined linkage-physical map of the human genome," Am. J. Hum. Genet., vol. 75, 2004, pp. 1143-1148.
Kong, et al., "A high-resolution recombination map of the human genome" Nature Genetics, vol. 31, Jul. 2002, pp. 241-247.
Kong, et al., "Allele-sharing models—LOD scores and accurate linkage tests" Am. J. Hum. Genet. 61, (1997) pp. 1179-1188.

(56) References Cited

OTHER PUBLICATIONS

Kruglyak, et al., "Complete Multipoint Sib-Pair Analysis of Qualitative and Quantitative Traits" Am. J. Hum. Genet. 57, (1995) pp. 439-454.
Kruglyak, et al., "Faster multipoint linkage analysis using Fourier transforms" J. Comput. Biol. 5, (1998) pp. 1-7.
Kruglyak, et al., "Linkage thresholds for two-stage genome scans" Am. J. Hum. Genet. 62, (1998) pp. 994-997.
Kruglyak, et al., "Parametric and Nonparametric Linkage Analysis: A Unified Multipoint Approach" Am. J. Hum. Genet. 58, (1996) pp. 1347-1363.
Kruglyak, et al., "Rapid Multipoint Linkage Analysis of Recessive Traits in Nuclear Families, Including Homozygosity Mapping" Am. J. Hum. Genet. 56 (1995) pp. 519-527.
Kruglyak, L., "The use of a genetic map of biallelic markers in linkage studies" Nat. Genet. 17, (1997) pp. 21-24.
Kumar, et al., "Recurrent 16p11.2 microdeletions in autism" Human Molecular Genetics, 2008, vol. 17, No. 4, pp. 628-638.
Laberge, et al., "Population history and its impact on medical genetics in Quebec" Clin. Genet. 68 (2005) pp. 287-301.
Lafrate, et al., "Detection of large-scale variation in the human genome," Nature Genetics, vol. 36, No. 9, Sep. 2004, pp. 949-951.
Lander, et al., "Construction of multilocus genetic linkage maps in humans" Genetics, vol. 84, Apr. 1987, pp. 2363-2367.
Lander, et al., "Genetic dissection of complex traits: guidelines for interpreting and reporting linkage results" Nat. Genet. 11, (1995) pp. 241-247.
Lander, et al., "Homozygosity mapping: a way to map human recessive traits with the DNA of inbred children" Science 236, (1987) pp. 1567-1570.
Lange, et al., "Extensions to pedigree analysis I. Likelihood calculations for simple and complex pedigrees" Hum. Hered. 25 (1975) pp. 95-105.
Leclair, et al., "Enhanced kinship analysis and STR-based DNA typing for human identification in mass fatality incidents: The Swissair Flight 111 disaster" Journal of Forensic Sciences, 49(5) (2004) pp. 939-953.
Leibon, et al., "A simple computational method for the identification of disease-associated loci in complex, incomplete pedigrees" arXiv:0710:5625v1 [q-bio.GN] Oct. 30, 2007, pp. 1-20.
Leibon, et al.,"A SNP Streak Model for the Identification of Genetic Regions Identical-by-descent" Statistical Applications in Genetics and Molecular Biology, vol. No. 1, Article 16 (2008) pp. 1-17.
Leutenegger, et al., "Estimation of the Inbreeding Coefficient through Use of Genomic Data," Am. J. Hum. Genet. 73, Jul. 29, 2003, pp. 516-523.
Leutenegger, et al., "Using genomic inbreeding coefficient estimates for homozygosity mapping of rare recessive traits: Application to Taybi-Linder syndrome" Am. J. Hum. Genet., vol. 79, Jul. 2006, pp. 62-66.
Li, et al., "Fast and accurate long-read alignment with Burrows-Wheeler transform" Bioinformatics vol. 26, No. 5, 2010, pp. 589-595.
Li, et al., "Joint modeling of linkage and association: identifying SNPs responsible for a linkage signal" Am. J. Hum. Genet. 76 (2005) pp. 934-949.
Li, et al., "Mapping short DNA sequencing reads and calling variants using mapping quality scores," Genome Research, Aug. 19, 2008, pp. 1851-1858. <doi: 10.1101/gr.078212.108>.
Li, et al., "Modeling linkage disequilibrium and identifying recombination hotspots using single-nucleotide polymorphism data" Genetics 165, (2003) pp. 2213-2233.
Li, et al., "Similarity of DNA fingerprints due to chance and relatedness" Hum. Hered. 43, 1993 pp. 45-52.
Li, et al., "The sequence alignment/map format and SAMtools" Bioinformatics vol. 25, No. 16 (2009) pp. 2078-2079.
Lien, et al. "Evidence for heterogeneity in recombination in the human pseudoautosomal region: High resolution analysis by sperm typing and radiation-hybrid mapping" Am. J. Hum. Genet. 66, 2000, pp. 557-566.
Lin, et al. "Haplotype inference in random population samples" Am. J. Hum. Genet. 71, 2002, pp. 1129-1137.
Liu, et al., "Affected sib-pair test in inbred populations" Ann. Hum. Genet. 68, (2004) pp. 606-619.
Long, et al., "An E-M Algorithm and Testing Strategy for Multiple-Locus Haplotypes" Am. J. Hum. Genet. 56 (1995) pp. 799-810.
Lowe, et al., "Genome-Wide Association Studies in an Isolated Founder Population from the Pacific Island of Kosrae," PLoS Genet 5(2), 2009, e1000365, pp. 1-17. <doi:10.1371/journal.pgen. 1000365>.
Lynch, et al., "Analysis of population genetic structure with RAPD markers" Molecular Ecology, 3, (1994) pp. 91-99.
Lynch, et al., "Estimation of pairwise relatedness with molecular markers" Genetics, vol. 152, (1999) pp. 1753-1766.
Lynch, M., "Estimation of relatedness by DNA fingerprinting" Molecular and Biological Evolution, 5, (1988) pp. 584-599.
Ma, et al., "PatternHunter: faster and more sensitive homology search" Bioinformatics, vol. 18, No. 3 (2002) pp. 440-445.
Mao, et al., "A Monte Carlo algorithm for computing the IBD matrices using incomplete marker information" Heredity (2005) 94, pp. 305-315.
Marchini, et al., "A comparison of phasing algorithms for trios and unrelated individuals," Am. J. Hum. Genet. 78, 2006, pp. 437-450.
Matsuzaki, et al., "Genotyping over 100,000 SNPs on a pair of oligonucleotide arrays" Nat. Methods, vol. 1, No. 2, Nov. 2004, pp. 109-111.
Matsuzaki, et al., "Parallel genotyping of over 10,000 SNPs using a one-primer assay on a high-density oligonucleotide array" Genome Res., vol. 14, No. 3, Mar. 2004, pp. 414-425.
McPeek, et al., "Statistical test for detection of misspecified relationships by use of genome-screen data" Am. J. Hum. Genet. 66, (2000) pp. 1076-1094.
Meuwissen, et al., "Fine mapping of a quantitative trait locus for twinning rate using combined linkage and linkage disequilibrium mapping," Genetics 161 (2002) pp. 373-379.
Meuwissen, et al., "Multipoint Identity-by-Descent Prediction Using Dense Markers to Map Quantitative Trait Loci and Estimate Effective Population Size," Genetics 176, Aug. 2007, pp. 2551-2560.
Meuwissen, et al., "Prediction of identity by descent probabilities from marker-haplotypes," Genetics Selelction Evolution, vol. 33, Nov. 15, 2001, pp. 605-634. <doi: 10.1186/1297-9686-33-6-605>.
Miano, et al., "Pitfalls in homozygosity mapping" Am. J. Hum. Genet. 67, (2000) pp. 1348-1351.
Milligan, B.G., "Maximum-Likelihood Estimation of Relatedness" Genetics 163, (2003) pp. 1153-1167.
Miyazawa et al., "Homozygosity Haplotype Allows a Genomewide Search for the Autosomal Segments Shared among Patients," Am. J. Hum. Genet. Vol. 80, Jun. 2007, pp. 1090-1102.
Morris, et al., "The avuncular index and the incest index" Advances in Forensic Haemogenetics 2, (1988) pp. 607-611.
Morton, N.E., "Sequential test for the detection of linkage" Am. J. Hum. Genet. 7 (1955) pp. 277-318.
Motro, et al., "The affected sib method. I. Statistical features of the affected sib-pair method" Genetics 110, (1985) pp. 525-538.
Nelson, et al., "Genomic mismatch scanning: A new approach to genetic linkage mapping" Nature Genetics, vol. 4, May 1993, pp. 11-18.
Newton, et al., "Inferring the location and effect of tumor suppressor genes by instability-selection modeling of allelic-loss data" Biometrics 56, (2000) pp. 1088-1097.
Newton, et al., "On the statistical analysis of allelic-loss data" Statistics in Medicine 17, (1998) pp. 1425-1445.
Ning et al., "SSAHA: A Fast Search Method for Large DNA Databases," Genome Research, Oct. 2001, vol. 11, No. 10, pp. 1725-1729.
Nyholt, Dale R., "Genehunter: Your 'One-Stop Shop' for Statistical Genetic Analysis?" Hum. Hered. 53 (2002) pp. 2-7.
O'Connell, J.R., "Rapid multipoint linkage analysis via inheritance vectors in the Elston-Stewart algorithm" Hum. Hered. 51, (2001) pp. 226-240.
O'Connell, J.R., "The VITESSE algorithm for rapid exact multilocus linkage analysis via genotype set-recoding and fuzzy inheritance" Nature. Genet. 11, (1995) pp. 402-408.

(56) References Cited

OTHER PUBLICATIONS

Oliehoek, et al., "Estimating relatedness between individuals in general populations with a focus on their use in conservation programs" Genetics 173 (2006) pp. 483-496.

Olson, et al., "Relationship estimation by Markov-process models in sib-pair linkage study" Am. J. Hum. Genet. 64, (1999) pp. 1464-1472.

Opposition to Defendants' Motion to Dismiss Plaintiff's Complaint, filed in the United States District Court in and for the Northern District of California LLC on Jul. 13, 2018, Case No. 18-cv-02791-JCS, Re 23andMe, Inc. v. Ancestry.com DNA, LLC, Ancestry.com Operations Inc., and Ancestry.com.

Order Granting In Part and Denying In Part Defendants' Motion to Dismiss, dated Aug. 23, 2018, Case No. 18-cv-02791-JCS, from the United States District Court in and for the Northern District of California LLC, Re 23andMe, Inc. v. Ancestry.com DNA, LLC, Ancestry.com Operations Inc., and Ancestry.com.

Patterson, et al., "Population Structure and Eigenanalysis," PLoS Genetics, vol. 2, No. 12, e190, Dec. 2006, pp. 2074-2093.

Paynter, et al., "Accuracy of Multiplexed Illumina Platform-Based Single-Nucleotide Polymorphism Genotyping Compared between Genomic and Whole Genome Amplified DNA Collected from Multiple Sources," Cancer Epidemiol Biomarkers Prev. 15, Dec. 2006, pp. 2533-2536.

Pemberton et al., "Inference of unexpected Genetic relatedness among individuals in HapMap phase III" Am. J. Hum. Genet. 87, (2010) pp. 457-464.

Perry, et al., "The fine-scale and complex architecture of human copy-number variation," Am. J. Hum. Genet. 82, Mar. 2008, pp. 685-695.

Pinto, et al., "Copy-number variation in control population cohorts," Human Molecular Genetics, 2007, vol. 16, review issue No. 2, pp. R168-R173. <doi:10.1093/hmg/ddm241>.

Porras-Hurtado, et al., "An overview of Structure: applications, parameter settings, and supporting software," Frontiers in Genetics, vol. 4, No. 96, May 29, 2013, pp. 1-13.

Pritchard, et al., "Association Mapping in Structured Populations," Am. J. Hum. Genet., vol. 67, 2000, pp. 170-181.

Pritchard, et al., "Inference of population structure using multilocus genotype data" Genetics 155, (2000) pp. 945-959.

Purcell, et al., "PLINK: A Tool Set for Whole-Genome Association and Population-Based Linkage Analysis," The American Journal of Human Genetics, vol. 81, Sep. 2007, pp. 559-575.

Queller, et al., "Estimating relatedness using genetic markers" Evolution, vol. 43, No. 2, (1989) pp. 258-275.

Rabiner, L., "A Tutorial on Hidden Markov Models and Selected Applications in Speech Recognition," Proceedings of the IEEE, vol. 77, No. 2, Feb. 1989, pp. 257-286.

Rannala, et al., "Detecting immigration by using multilocus genotypes" Proc. Natl. Acad. Sci. USA 94, (1997) pp. 9197-9201.

Rastas, et al., "A hidden Markov technique for haplotype reconstruction" Lect. Notes Comput. Sci. 3692, (2005) pp. 140-151.

Redon, et al., "Global variation in copy number in the human genome," Nature vol. 444, Nov. 23, 2006, pp. 444-454. <doi:10.1038/nature05329>.

Reid, et al., "Specificity of sibship determination using the ABI identifier multiplex system" J. Forensic Sci. 49, (2004) pp. 1262-1264.

Reply Brief of Appellant 23AndMe, Inc., Case No. 2019-1222, Document: 25, Filed on Apr. 8, 2019, In The US Court of Appeals for Federal Circuit, pp. 1-38.

Riquet, J. et al., "Fine-mapping of quantitative trait loci by identity by descent in outbred populations: application to milk production in dairy cattle," Proceedings of the National Academy of Sciences, vol. 96, No. 16, Aug. 3, 1999, pp. 9252-9257. <doi: 10,1073/pnas.96.16.9252>.

Risch, et al., "Linkage strategies for genetically complex traits. II. The power of affected relative pairs" Am. J. Hum. Genet. 46 (1990) pp. 229-241.

Risch, N., "Linkage Strategies for Genetically Complex Traits. II. The Power of Affected Relative Pairs" Am. J. Hum. Genet. 46, (1990 a,b) pp. 222-241.

Ritland, et al., "Inferences about quantitative inheritance based on natural population structure in the yellow monkeyflower, *Mimulus Guttatus*" Evolution 50, (1996) pp. 1074-1082.

Ritland, K., "A marker-based method for inferences about quantitative inheritance in natural populations" Evolution 50, (1996b) pp. 1062-1073.

Ritland, K., "Estimators for pairwise relatedness and individual inbreeding coefficients" Genet. Res. 67 (1996a) pp. 175-185.

Ritland, K., "Marker-inferred relatedness as a tool for detecting heritability in nature" Mol. Ecol. 9, (2000) pp. 1195-1204.

Sanda, et al., "Genomic analysis I: inheritance units and genetic selection in the rapid discovery of locus linked DNA makers" Nucleic Acids Research, vol. 14, No. 18 (1986) pp. 7265-7283.

Schaid, et al., "Caution on pedigree haplotype inference with software that assumes linkage equilibrium" Am. J. Hum. Genet. 71, (2002) pp. 992-995.

Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.

Schork, N.J., "Extended Multipoint Identity-by-Descent Analysis of Human Quantitative Traits: Efficiency, Power, and Modeling Considerations" Am. J. Hum. Genet. 53 (1993) pp. 1306-1319.

Shmulewitz, et al., "Linkage analysis of quantitative traits for obesity, diabetes, hypertension, and dyslipidemia on the island of Kosrae, Federated States of Micronesia," Proc. Natl. Acad. Sci. vol. 103, No. 10, Mar. 7, 2006, pp. 3502-3509.

Shore, et al., "A recurrent mutation in the BMP type I receptor ACVR1 causes inherited and sporadic fibrodysplasia ossificans progressiva" Nat. Genet. 38 (2006) pp. 525-527.

Siegmund, et al., "Statistical Analysis of Direct Identity-by-descent Mapping," Annals of Human Genetics (2003) 67,464-470.

Slager, et al., "Evaluation of candidate genes in case-control studies: a statistical method to account for related subjects" Am. J. Hum. Genet. 68, (2001) pp. 1457-1462.

Smouse, et al., "A genetic mixture analysis for use with incomplete source population data" Can J Fisheries Aquatic Sci. 47 (1990) pp. 620-634.

Sobel, et al., "Descent graphs in pedigree analysis: Applications to haplotyping, location scores, and marker-sharing statistics" Am. J. Hum. Genet. 58, (1996) pp. 1323-1337.

Stam, P., "The distribution of the fraction of the genome identical by descent in finite random mating populations" Genet. Res. Camb. 35, (1980) pp. 131-155.

Stephens, et al., "A Comparison of Bayesian Methods for Haplotype Reconstruction from Population Genotype Data," Am. J. Hum. Genet., vol. 73, 2003, pp. 1162-1169.

Stephens, et al., "A New Statistical Method for Haplotype Reconstruction from Population Data," Am. J. Hum. Genet., vol. 68, 2001, pp. 978-989.

Stephens, et al., "Accounting for Decay of Linkage Disequilibrium in Haplotype Inference and Missing-Data Imputation," Am. J. Hum. Genet., vol. 76, 2005, pp. 449-462.

Stone, et al., "DELRIOUS: a computer program designed to analyze molecular marker data and calculate delta and relatedness estimates with confidence" Molecular Ecology Notes, vol. 1, (2001) pp. 209-212.

Tang, et al., "Estimation of individual admixture: Analytical and study design considerations" Genet. Epidem. 28, (2005) pp. 289-301.

Te Meerman, et al., "Genomic Sharing Surrounding Alleles Identical by Descent: Effects of Genetic Drift and Population Growth" Genetic Epidemiology vol. 14 (1997) pp. 1125-1130.

Teo, et al., "Singapore Genome Variation Project: A haplotype map of three Southeast Asian populations" Genome Res. 19, (2009) pp. 2154-2162.

The International HapMap Consortium, "A haplotype map of the human genome" vol. 437, Oct. 27, 2005, pp. 1300-1320. <doi:10.1038/nature04226>.

(56) References Cited

OTHER PUBLICATIONS

The International HapMap Consortium, "A haplotype map of the human genome," Nature, vol. 437, Oct. 27, 2005, pp. 1299-1320. <doi:10.1038/nature04226>.
The International HapMap Consortium, "A second generation human haplotype map of over 3.1 million SNPs," Nature, vol. 449, Oct. 18, 2007, pp. 851-860. <doi: 10.1038/nature06258>.
Thomas, et al., "Genomic mismatch scanning in pedigrees" IMA Journal of Mathematics Applied in Medicine and Biology, vol. 11, (1994) pp. 1-16.
Thomas, et al., "Multilocus linkage analysis by blocked Gibbs sampling" Statistics and Computing, vol. 10, (2000), pp. 259-269.
Thomas, et al., "Shared genomic segment analysis. Mapping disease predisposition genes in extended pedigrees using SNP genotype assays," Ann. Hum. Genet. 72, Mar. 2008, pp. 279-287.
Thompson, E.A., "Estimation of relationships from genetic data" In Handbook of Statistics, vol. 8, (1991) pp. 255-269.
Thompson, E.A., "Inference of genealogical structure" Soc. Sci. Inform. 15, (1976) pp. 477-526.
Thompson, E.A., "The estimation of pairwise relationships" Ann. Hum. Genet., Lond. 39,(1975) pp. 173-188.
Thompson, et al., "The IBD process along four chromosomes," Theor. Popul. Biol. May 73(3) May 2008, pp. 369-373.
Tishkoff, et al., "The Genetic Structure and History of Africans and African Americans," Science, vol. 324(5930), May 22, 2009, pp. 1035-1044. <doi:10.1126/science.1172257>.
Todorov, et al., "Probabilities of identity-by-descent patterns in sibships when the parents are not genotyped" Genet. Epidemiol, 14 (1997) pp. 909-913.
Transcript of Proceedings dated Aug. 16, 2018, Case No. 18-cv-02791-JCS, Re Defendant's Motion to Dismiss, heard in the United States District Court in and for the Northern District of California LLC, in the matter of *23andMe, Inc. v. Ancestry.com DNA, LLC, Ancestry.com Operations Inc., and Ancestry.com.*
Tu, et al., "The maximum of a function of a Markov chain and application to linkage analysis" Adv. Appl. Probab. 31, (1999) pp. 510-531.
Tzeng, et al., "Determination of sibship by PCR-amplified short tandem repeat analysis in Taiwan" Transfusion 40, (2000) pp. 840-845.
Van De Casteele, et al., "A comparison of microsatellite-based pairwise relatedness estimators" Molecular Ecology 10, (2001) pp. 1539-1549.
Wang, et al., "An estimator of pairwise relatedness using molecular markers" Genetics, vol. 160 (2002) pp. 1203-1215.
Wang, et al., "An integrated hidden Markov model designed for high-resolution copy number variation detection in whole-genome SNP genotyping data," Genome Res. 17, 2007, pp. 665-1674.
Weir, et al., "A maximum-likelihood method for the estimation of pairwise relatedness in structured populations" Genetics 176, (2007) pp. 421-440.
Weir, et al., "Allelic association patterns for a dense SNP map" Genetic Epidemiology 24, (2004) pp. 442-450.
Weir, et al., "Behavior of pairs of loci in finite monoecious populations" Theor. Popul. Biol. 6 (1974) pp. 323-354.
Weir, et al., "Estimating F-statistics" Annual Review of Genetics, 36, (2002) pp. 721-750.
Weir, et al., "Genetic relatedness analysis: modem data and new challenges" Nature Genetics 7, (2006) pp. 771-780.
Weir, et al., "Group inbreeding with two linked loci" Genetics 63 (1969) pp. 711-742.
Weir, et al., "Measures of human population structure show heterogeneity among genomic regions" Genome Res. 15 (2005) pp. 1468-1476. [PubMed: 16251456].
Weiss, et al., "Association between microdeletion and microduplication at 16p11.2 and autism" New England Journal of Medicine, vol. 358, No. 7, Feb. 14, 2008, pp. 667-675.
Whittemore, et al., "A Class of Tests for Linkage Using Affected Pedigree Members" Biometrics 50, (1994) pp. 118-127.
Wijsman, et al., "Multipoint linkage analysis with many multiallelic or dense diallelic markers: Markov chain-Monte Carlo provides practical approaches for genome scans on general pedigrees" Am. J. Hum. Genet. 79, (2006) pp. 846-858.
Wright, S. "Systems of Mating. I. The Biometric Relations Between Parent and Offspring," Genetics, 6:111.
Yu, et al., "A unified mixed-model method for association mapping accounting for multiple levels of relatedness" Nature Genet. 38, (2006) pp. 203-208.
Zhang, et al., "A comparison of several methods for haplotype frequency estimation and haplotype reconstruction for tightly linked markers from general pedigrees" Genet. Epidemiol. 30 (2006) pp. 423-437.
Zhao et al., "On Relationship Inference Using Gamete Identity by Descent Data", Journal of Computational Biology, vol. 8, No. 2, Nov. 2, 2001, pp. 191-200.
U.S. Appl. No. 12/774,546, filed May 5, 2010, Macpherson et al.
Office Action dated Jan. 3, 2014 in U.S. Appl. No. 12/774,546.
Final Office Action dated Jan. 8, 2015 in U.S. Appl. No. 12/774,546.
Office Action dated Aug. 12, 2015 in U.S. Appl. No. 12/774,546.
Final Office Action dated Feb. 2, 2016 in U.S. Appl. No. 12/774,546.
Office Action dated Feb. 1, 2017 in U.S. Appl. No. 12/774,546.
Notice of Allowance dated Jan. 21, 2021 in U.S. Appl. No. 17/073,095.
Notice of Allowance dated Jan. 7, 2021 in U.S. Appl. No. 17/073,110.
Office Action dated Dec. 24, 2020 in U.S. Appl. No. 17/073,122.
Office Action dated Feb. 3, 2021 in U.S. Appl. No. 17/073,128.
European Examination Report dated Apr. 21, 2020 in Application No. EP 17172048.5.
Hon, et al., "Discovering Distant Relatives within a Diverse Set of Populations Using DNA Segments Identical by Descent" *Advancing Human Genetics & Genomics Annual Meeting Poster Session*, Oct. 20, 2009, 23andMe, Inc., pp. 1-2.
*23Andme, Inc., v. ancestry.com DNA, LLC, ancestry.com Operations Inc., ancestry.com LLC*, No. 2019-1222, United States Court of Appeals for the Federal Circuit, Petition For Rehearing En Banc, filed Nov. 4, 2019, Case No. 18-cv-02791-EMC, pp. 1-28.
*23Andme, Inc., v. ancestry.com DNA, LLC, ancestry.com Operations Inc., ancestry.com LLC*, No. 2019-1222, United States Court of Appeals for the Federal Circuit, Defendant's-Appellees' Response to Appellant 23ANDME, Inc.'S Petition for Rehearing En Banc, filed Dec. 19, 2019, Case No. 18-cv-02791-EMC, pp. 1-25.
*23Andme, Inc., v. ancestry.com DNA, LLC, ancestry.com Operations Inc., ancestry.com LLC*, No. 2019-1222, United States Court of Appeals for the Federal Circuit, On Petition For Rehearing En Banc; Order, denied; filed Jan. 9, 2020, Case No. 18-cv-02791-EMC, pp. 1-2.
Jiang, et al., "An efficient parallel implementation of the hidden Markov methods for genomic sequence-search on a massively parallel system." IEEE Transactions on Parallel and Distributed Systems 19.1 (2008) pp. 15-23.
Lavenier, Dominique, and J-L. Pacherie. "Parallel processing for scanning genomic data-bases." Advances in Parallel Computing, vol. 12, North-Holland, 1998, pp. 81-88.
Final Office Action dated Jun. 14, 2021 in U.S. Appl. No. 17/073,122.
Final Office Action dated Jun. 30, 2021 in U.S. Appl. No. 17/073,128.
Office Action dated Jun. 8, 2021 in U.S. Appl. No. 17/301,129.
U.S. Appl. No. 17/351,052, filed Jun. 17, 2021, Hon et al.
Office Action dated Apr. 23, 2021 in U.S. Appl. No. 16/129,645.
Notice of Allowance dated Apr. 29, 2021 in U.S. Appl. No. 17/073,110.
Borsting et al. "Performance of the SNPfor1D 52 SNP-plex assay in paternity testing," (Forensic Science International, vol. 2 (2008) pp. 292-300.
Nuanmeesri, et al., "Genealogical Information Searching System" 2008 4th IEEE International Conference on Management of Innovation and Technology. IEEE, 2008, pp. 1255-1259.
Abe, H. et al., "Implementing an Integrated Time-Series Data Mining Environment Based on Temporal Pattern Extraction Methods: A Case Study of an Interferon Therapy Risk Mining for Chronic Hepatitis", New Frontiers in Artificial Intelligence, Lecture Notes in Computer Science, vol. 4012, Jun. 2005, pp. 425-435.
Anonymous , "Frequency" (Web Definition ) , Feb. 24, 2011, Wikipedia, Harvard School of Public Health | Harvard Center for

(56) References Cited

OTHER PUBLICATIONS

Cancer Prevention , "Your Disease Risk" website for calculating disease risk , 34 exemplary pages submitted including heart disease risk estimation and listings of risk factors , last accessed via the world wide web on Apr. 30, 2007, at the URL address:http://www.yourdiseaserisk.harvard.edu/english/index.htm).

Batzoglou, S. et al., "Human And Mouse Gene Structure: Comparative Analysis and Application to Exon Prediction", Genome Research, Cold Spring Harbor Laboratory Press, vol. 10, No. 7, Jul. 2000, pp. 952-958.

Carson, R.C. et al . , Abnormal Psychology and Modern Life , 8th edition, Scott Foresman and Company, Glenview , IL , 1988, pp. 56-57.

Cespivova, H., "Roles of Medical Ontology in Association Mining CRISP-DM Cycle", Proceedings of the ECML/PKDD04 Workshop on Knowledge Discovery and Ontologies, PISA, 2004, pp. 12.

Cooper, D.N. et al., "The Mutational Spectrum Of Single Base-Pair Substitutions Causing Human Genetic Disease: Patterns And Predictions", Human Genetics, vol. 85, No. 1, Jun. 1990, pp. 55-74.

Das, S., "Filters, Wrappers And a Boosting-Based Hybrid For Feature Selection", In Proceedings Of The Eighteenth International Conference On Machine Learning, Jun. 28, 2001, pp. 74-81.

Duan, K.B. et al., "Multiple SVM-RFE For Gene Selection In Cancer Classification With Expression Data", IEEE Transactions On Nanobioscience, vol. 4, No. 3, Aug. 29, 2005, pp. 228-234.

EP Office action dated Oct. 27, 2021, in EP Application No. EP17172048.5.

Hitsch, G.J. et al., "What Makes You Click ?—Mate Preference and Matching Outcomes in Online Dating", MIT Sloan Research, Apr. 2006, pp. 603-606.

Klein, T.E. et al., "Integrating Genotype And Phenotype Information: An Overview Of The PharmGKB Project", The Pharmacogenetics Journal, vol. 1, No. 3, 2001, pp. 167-170.

Mani, S. et al., "Causal Discovery From Medical Textual Data", 2000, pp. 542-546.

Miyamoto, K et al., "Diagnostic and Therapeutic Applications of Epigenetics", Japanese Journal of Clinical Oncology, Keigakul Publishing Company, vol. 35, No. 6, Jun. 1, 2005, pp. 293-301.

Nadkarni, P.M. et al., "Data Extraction And Ad Hoc Query Of An Entity-Attribute-Value Database", Journal of the American Medical Informatics Association, vol. 5, No. 6, Nov.-Dec. 1998, pp. 511-527.

Nielsen, O.T. et al., "Molecular Characterization Of Soft Tissue Tumours: A Gene Expression Study", The Lancet, vol. 359, Apr. 13, 2002, pp. 1301-1307.

Peedicayil, J., "Epigenetic Therapy—a New Development in Pharmacology", Indian Journal of Medical Research, vol. 123, No. 1, Jan. 2006, pp. 17-24.

Prather, J.C. et al., "Medical Data Mining: Knowledge Discovery In A Clinical Data Warehouse", Proceedings Of The AMIA Annual Fall Symposium, 1997, pp. 101-105.

Roddick, J.F. et al., "Exploratory Medical Knowledge Discovery: Experiences And Issues", vol. 5, No. 1, Jul. 1, 2003, ACM, pp. 94.99.

Smith., "SNPs and Human Disease", Nature, vol. 435, Jun. 2005, pp. 993.

Stadler, E.L, et al., "Personality Traits and Platelet Monoamine Oxidase Activity in a Swedish Male Criminal Population", Neuropsychobiology, vol. 46, No. 4, 2002, pp. 202-208.

U.S. Non-Final Office Action dated Dec. 9, 2021, in U.S. Appl. No. 17/351,052.

U.S Notice of Allowance dated Mar. 4, 2022, in U.S. Appl. No. 17/351,052.

U.S. Appl. No. 17/576,738, inventors Hon et al., filed Jan. 14, 2022.

Vrbsky, S.V. et al., Approximate—a Query Processor That Produces Monotonically Improving Approximate Answers, IEEE Transactions on Knowledge and Data Engineering, vol. 5, No. 6, Dec. 1993, pp. 1056-1068.

Wagner, S.F., "Introduction To Statistics, Harper Collins Publishers", 1992, pp. 23-30.

U.S. Non-Final office Action dated Apr. 14, 2022 in U.S. Appl. No. 17/576,738.

U.S. Notice of Allowance dated Jul. 26, 2022, in U.S. Appl. No. 17/576,738.

* cited by examiner

```
Alice  A G T | C T G | C A A | ... -- 902
       C G A | C A G | T C A | ... -- 904

Bob    C A T | G A C | C C G | ... -- 906
       A A T | C T G | C A A | ... -- 908
```

FIG. 9

| Origin | Chromosome | Size |
|---|---|---|
| Ireland | 2 | 12.1 cM |
| Germany | 12 | 8.3 cM |
| Ireland | 14 | 14.7 cM |
| Ireland | 19 | 9.1 cM |

FIG. 13

| # Colocated Grandparents | Not from US, Canada | Including US, Canada |
|---|---|---|
| 4 | 1425 (15%) | 4179 (43%) |
| 3 | 436 (5%) | 1425 (15%) |
| 2 | 1956 (20%) | 2956 (31%) |
| 1 | 1649 (17%) | 1123 (12%) |
| 0 | 4217 (44%) | 0 (0%) |

ANCESTRY FINDER

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND OF THE INVENTION

Genealogy is the study of the history of families and the line of descent from ancestors. It is an interesting subject studied by many professionals as well as hobbyists. Traditional genealogical study techniques typically involve constructing family trees based on surnames and historical records. As gene sequencing technology becomes more accessible, there has been growing interest in genetic ancestry testing in recent years.

Existing genetic ancestry testing techniques are typically based on deoxyribonucleic acid (DNA) information of the Y chromosome (Y-DNA) or DNA information of the mitochondria (mtDNA). Aside from a small amount of mutation, the Y-DNA is passed down unchanged from father to son and therefore is useful for testing patrilineal ancestry of a man. The mtDNA is passed down mostly unchanged from mother to children and therefore is useful for testing a person's matrilineal ancestry. These techniques are found to be effective for identifying individuals that are related many generations ago (e.g., 10 generations or more), but are typically less effective for identifying closer relationships. Further, many relationships that are not strictly patrilineal or matrilineal cannot be easily detected by the existing techniques. In addition, improved techniques for inferring ancestry information for an individual would be desirable.

BRIEF DESCRIPTION OF THE DRAWINGS

Various embodiments of the invention are disclosed in the following detailed description and the accompanying drawings.

The patent or application file contains at least one drawing executed in color. Copies of this patent or patent application publication with color drawing(s) will be provided by the Patent and Trademark Office upon request and payment of the necessary fee.

FIGS. 4A-4I are screenshots illustrating user interface examples in connection with process 300.

FIG. 9 is a diagram illustrating an example in which phased data are compared to identify IBD.

FIG. 13 shows an interface example for a table view of an ancestry finder system.

FIG. 14 shows an interface example for the discovery view of a relative finder system that incorporates an ancestry finder system.

FIG. 16 shows an example of the effect of varying some of the settings in a karyotype view of an ancestry finder system.

DETAILED DESCRIPTION

Figure 1:
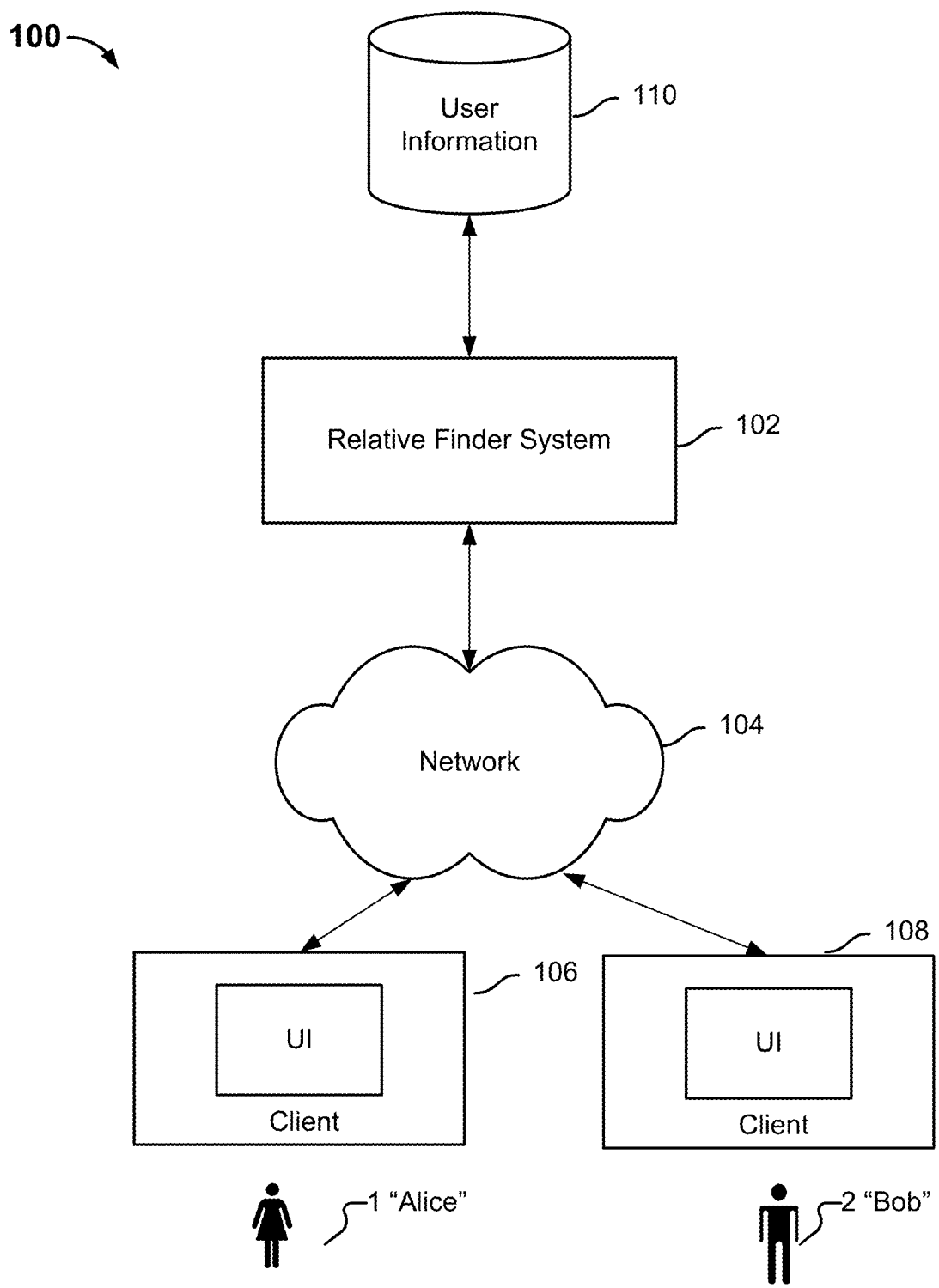
FIG. 1 is a block diagram illustrating an embodiment of a relative finding system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Because of recombination and independent assortment of chromosomes, the autosomal DNA and X chromosome DNA (collectively referred to as recombining DNA) from the parents is shuffled at the next generation, with small amounts of mutation. Thus, only relatives will share long stretches of genome regions where their recombining DNA is completely or nearly identical. Such regions are referred to as "Identical by Descent" (IBD) regions because they arose from the same DNA sequences in an earlier generation. The relative finder technique described below is based at least in part on locating IBD regions in the recombining chromosomes of individuals.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same or at least compatible indicate that the rest of the sequences, although not assayed directly, are also likely identical.

FIG. 1 is a block diagram illustrating an embodiment of a relative finding system. In this example, relative finder system 102 may be implemented using one or more server computers having one or more processors, one or more special purpose computing appliances, or any other appropriate hardware, software, or combinations thereof. The operations of the relative finder system are described in greater detail below. In this example, various users of the system (e.g., user 1 ("Alice") and user 2 ("Bob")) access the relative finder system via a network 104 using client devices such as 106 and 108. User information (including genetic information and optionally other personal information such as family information, population group, etc.) pertaining to the users is stored in a database 110, which can be implemented on an integral storage component of the relative finder system, an attached storage device, a separate storage device accessible by the relative finder system, or a combination thereof. Many different arrangements of the physical components are possible in various embodiments. In various embodiments, the entire genome sequences or assayed DNA markers (SNPs, STRs, CNVs, etc.) are stored in the database to facilitate the relative finding process. For example, approximately 650,000 SNPs per individual's genome are assayed and stored in the database in some implementations.

System 100 shown in this example includes genetic and other additional non-genetic information for many users. By comparing the recombining DNA information to identify IBD regions between various users, the relative finder system can identify users within the database that are relatives. Since more distant relationships (second cousins or further) are often unknown to the users themselves, the system allows the users to "opt-in" and receive notifications about the existence of relative relationships. Users are also presented with the option of connecting with their newly found relatives.

Figure 2:
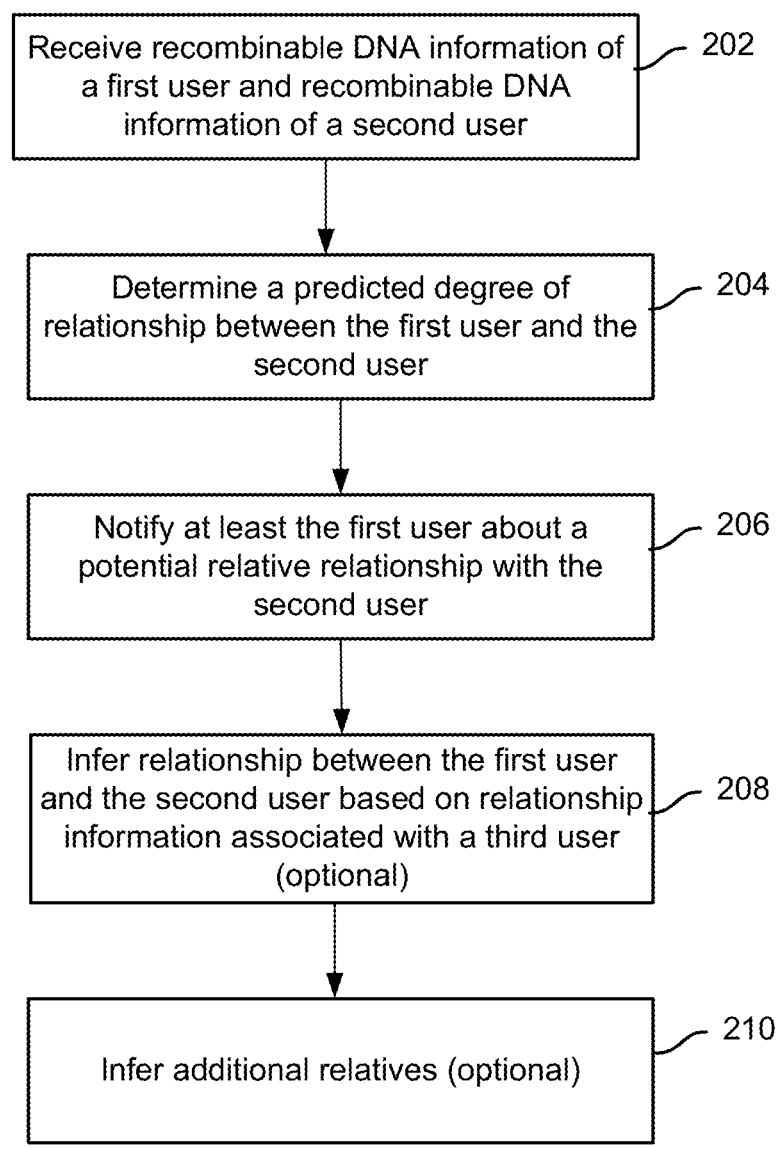
FIG. 2 is a flowchart illustrating an embodiment of a process for finding relatives in a relative finding system.

FIG. 2 is a flowchart illustrating an embodiment of a process for finding relatives in a relative finding system. Process 200 may be implemented on a relative finder system such as 100. The process may be invoked, for example, at a user's request to look for potential relatives this user may have in the database or by the system to assess the potential relationships among various users. At 202, recombining DNA information of a first user (e.g., Alice) and of a second user (e.g., Bob) is received. In some embodiments, the information is retrieved from a database that stores recombining DNA information of a plurality of users as well as any additional user information. For purposes of illustration, SNP information is described extensively in this and following examples. Other DNA information such as STR information and/or CNV information may be used in other embodiments.

At 204, a predicted degree of relationship between Alice and Bob is determined. In some embodiments, a range of possible relationships between the users is determined and a prediction of the most likely relationship between the users is made. In some embodiments, it is optionally determined whether the predicted degree of relationship at least meets a threshold. The threshold may be a user configurable value, a system default value, a value configured by the system's operator, or any other appropriate value. For example, Bob may select five generations as the maximum threshold, which means he is interested in discovering relatives with whom the user shares a common ancestor five generations or closer. Alternatively, the system may set a default value minimum of three generations, allowing the users to by default find relatives sharing a common ancestor at least three generations out or beyond. In some embodiments, the system, the user, or both, have the option to set a minimum threshold (e.g., two generations) and a maximum threshold (e.g., six generations) so that the user would discover relatives within a maximum number of generations, but would not be surprised by the discovery of a close relative such as a sibling who was previously unknown to the user.

At 206, Alice or Bob (or both) is notified about her/his relative relationship with the other user. In some embodiments, the system actively notifies the users by sending messages or alerts about the relationship information when it becomes available. Other notification techniques are possible, for example by displaying a list or table of users that are found to be related to the user. Depending on system settings, the potential relatives may be shown anonymously for privacy protection, or shown with visible identities to facilitate making connections. In embodiments where a threshold is set, the user is only notified if the predicted degree of relationship at least meets the threshold. In some embodiments, a user is only notified if both of the user and the potential relative have "opted in" to receive the notification. In various embodiments, the user is notified about certain personal information of the potential relative, the predicted relationship, the possible range of relationships, the amount of DNA matching, or any other appropriate information.

In some embodiments, at 208, the process optionally infers additional relationships or refines estimates of existing relationships between the users based on other relative relationship information, such as the relative relationship information the users have with a third user. For example, although Alice and Bob are only estimated to be $6^{th}$ cousins after step 204, if among Alice's relatives in the system, a third cousin, Cathy, is also a sibling of Bob's, then Alice and Bob are deemed to be third cousins because of their relative relationships to Cathy. The relative relationships with the third user may be determined based on genetic information and analysis using a process similar to 200, based on non-genetic information such as family tree supplied by one of the users, or both.

In some embodiments, the relatives of the users in the system are optionally checked to infer additional relatives at 210. For example, if Bob is identified as a third cousin of Alice's, then Bob's relatives in the system (such as children, siblings, possibly some of the parents, aunts, uncles, cousins, etc.) are also deemed to be relatives of Alice's. In some embodiments a threshold is applied to limit the relationships within a certain range. Additional notifications about these relatives are optionally generated.

Figure 3:
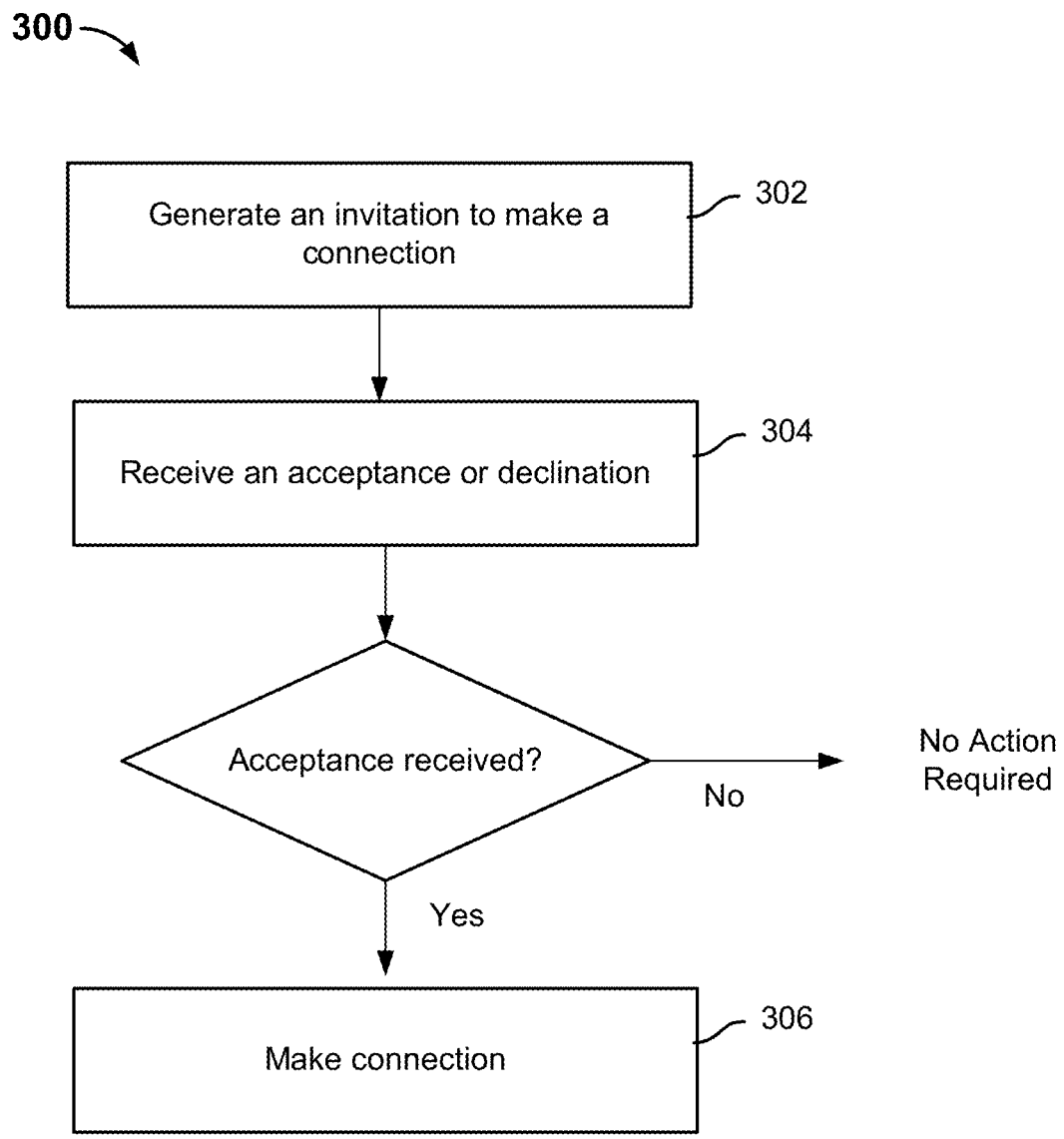
FIG. 3 is a flowchart illustrating an embodiment of a process for connecting a user with potential relatives found in the database.

Upon receiving a notification about another user who is a potential relative, the notified user is allowed to make certain choices about how to interact with the potential relative. FIG. 3 is a flowchart illustrating an embodiment of a process for connecting a user with potential relatives found in the database. The process may be implemented on a relative finder system such as 102, a client system such as 106, or a combination thereof. In this example, it is assumed that it has been determined that Alice and Bob are possibly 4th cousins and that Alice has indicated that she would like to be notified about any potential relatives within 6 generations. In this example, process 300 follows 206 of process 200, where a notification is sent to Alice, indicating that a potential relative has been identified. In some embodiments, the identity of Bob is disclosed to Alice. In some embodiments, the identity of Bob is not disclosed initially to protect Bob's privacy.

Upon receiving the notification, Alice decides that she would like to make a connection with the newly found relative. At 302, an invitation from Alice to Bob inviting Bob to make a connection is generated. In various embodiments, the invitation includes information about how Alice and Bob may be related and any personal information Alice wishes to share such as her own ancestry information. Upon receiving the invitation, Bob can accept the invitation or decline. At 304, an acceptance or a declination is received. If a declination is received, no further action is required. In some embodiments, Alice is notified that a declination has been received. If, however, an acceptance is received, at 306, a connection is made between Alice and Bob. In various embodiments, once a connection is made, the identities and any other sharable personal information (e.g., genetic information, family history, phenotype/traits, etc.) of Alice and Bob are revealed to each other and they may interact with each other. In some embodiments, the connection information is updated in the database.

In some embodiments, a user can discover many potential relatives in the database at once. Additional potential relatives are added as more users join the system and make their genetic information available for the relative finding process. FIGS. 4A-4I are screenshots illustrating user interface examples in connection with process 300. In this example, the relative finder application provides two views to the user: the discovery view and the list view.

Figure 4A:
Figure 4B:
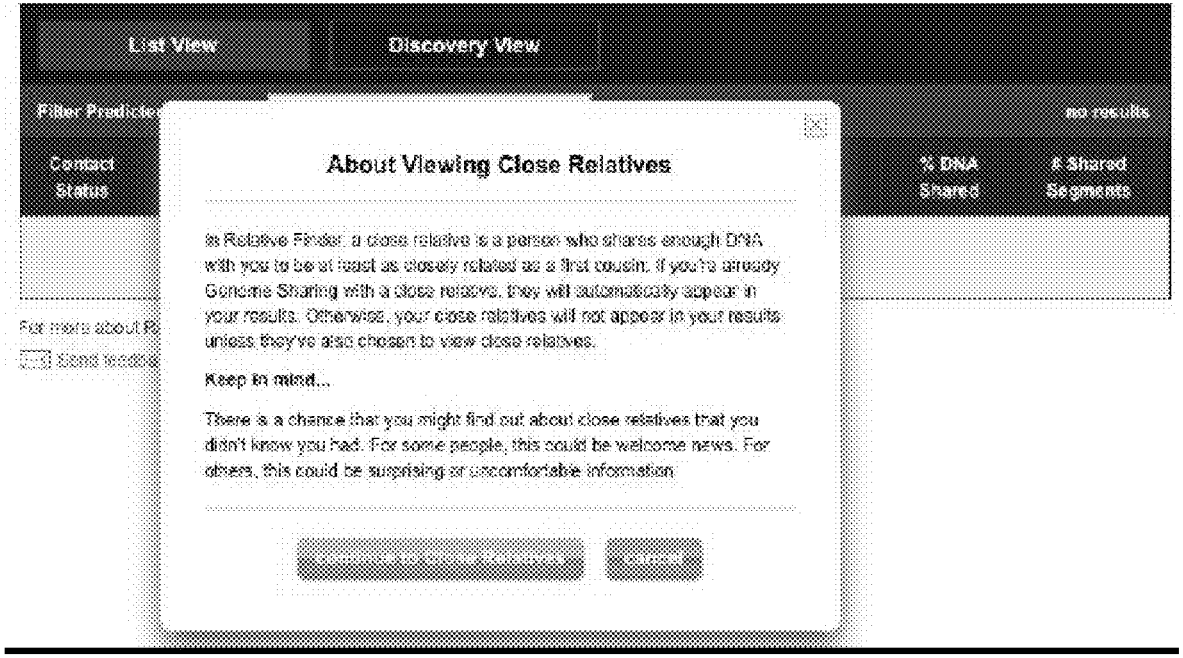

FIG. 4A shows an interface example for the discovery view at the beginning of the process. No relative has been discovered at this point. In this example, a privacy feature is built into the relative finder application so that close relative information will only be displayed if both the user and the close relative have chosen to view close relatives. This is referred to as the "opt in" feature. The user is further presented with a selection button "show close relatives" to indicate that he/she is interested in finding out about close relatives. FIG. 4B shows a message that is displayed when the user selects "show close relatives". The message explains to the user how a close relative is defined. In this case, a close relative is defined as a first cousin or closer. In other words, the system has set a default minimum threshold of three degrees. The message further explains that unless there is already an existing connection between the user and the close relative, any newly discovered potential close relatives will not appear in the results unless the potential close relatives have also chosen to view their close relatives. The message further warns about the possibility of finding out about close relatives the user did not know he/she had. The user has the option to proceed with viewing close relatives or cancel the selection.

Figure 4C:
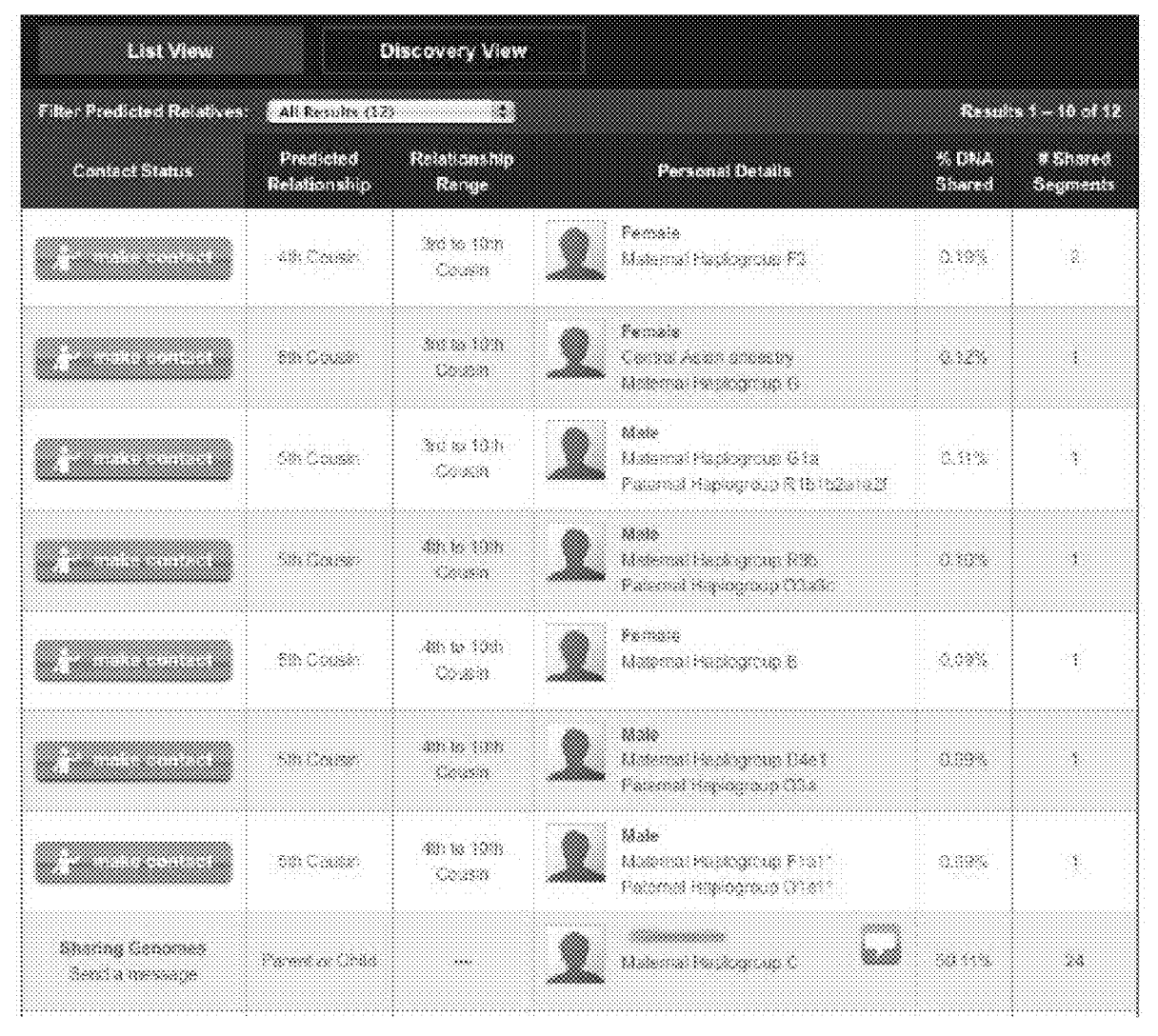

FIG. 4C shows the results in the discovery view. In this example, seven potential relatives are found in the database. The predicted relationship, the range of possible relationship, certain personal details a potential relative has made public, the amount of DNA a potential relative shares with the user, and the number of DNA segments the potential relative shares with the user are displayed. The user is presented with a "make contact" selection button for each potential relative.

Figure 4D:
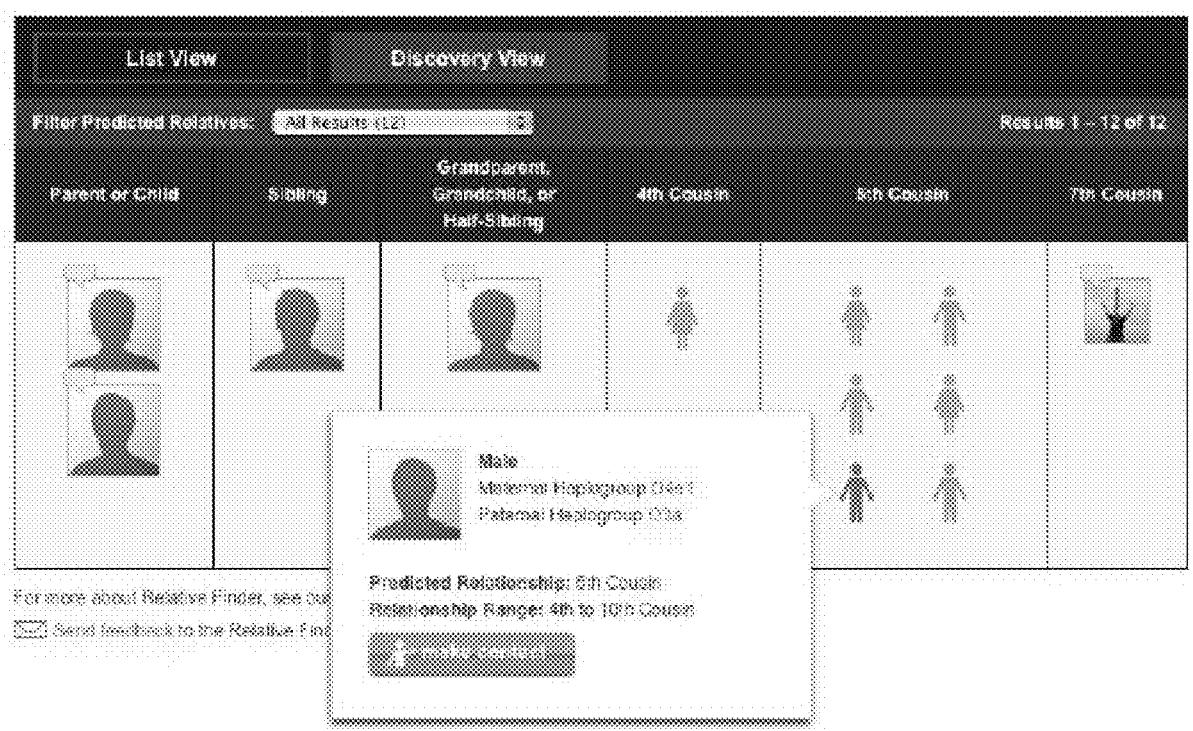

FIG. 4D shows the results in the list view. The potential relatives are sorted according to how close the corresponding predicted relationships are to the user in icon form. The user may select an icon that corresponds to a potential relative and view his/her personal information, the predicted relationship, relationship range, and other additional information. The user can also make contact with the potential relative.

Figure 4E:
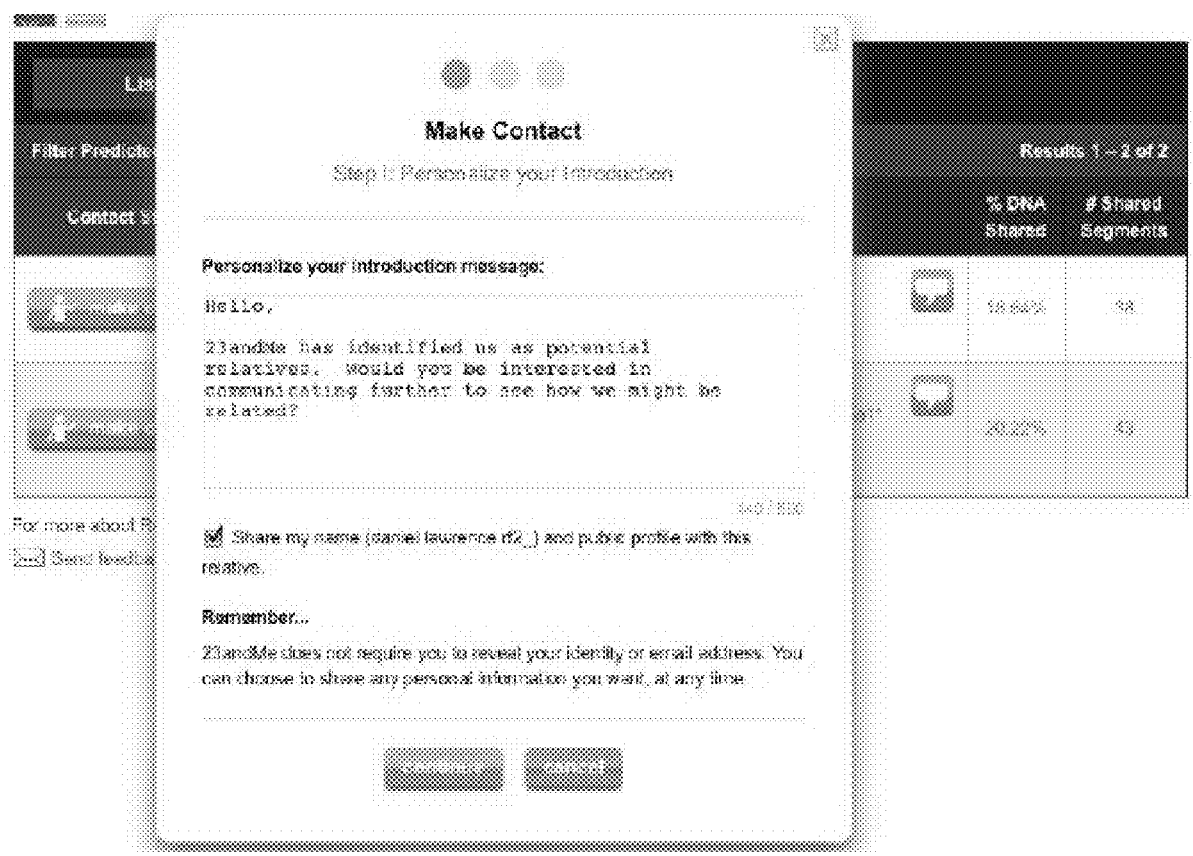
Figure 4F:
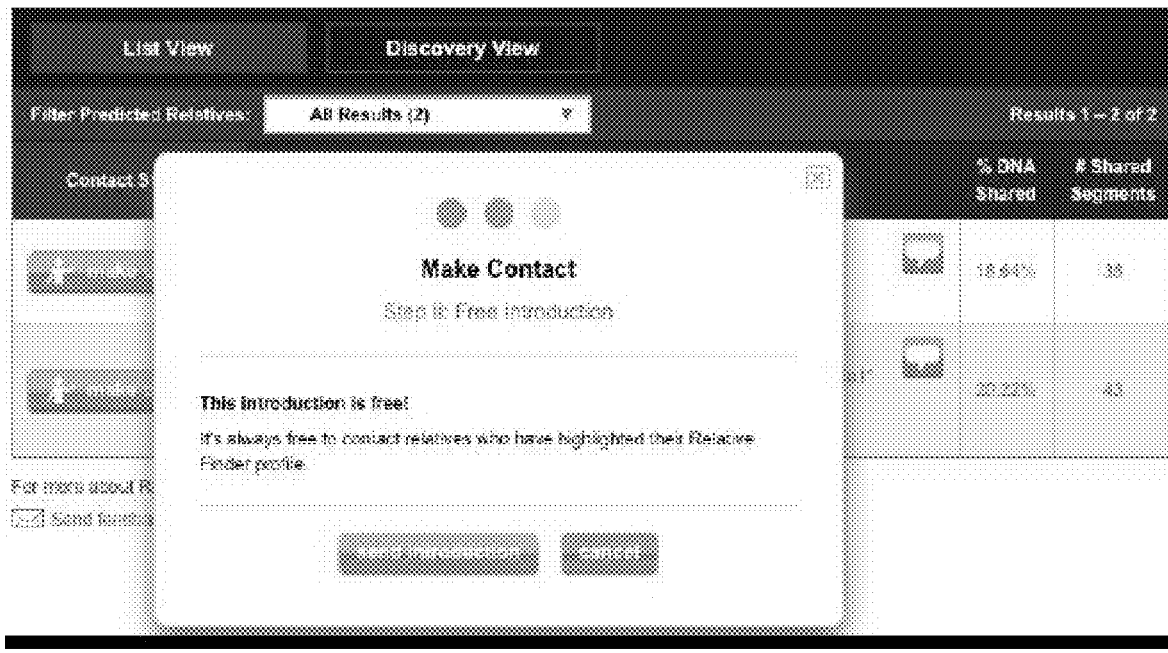
Figure 4G:
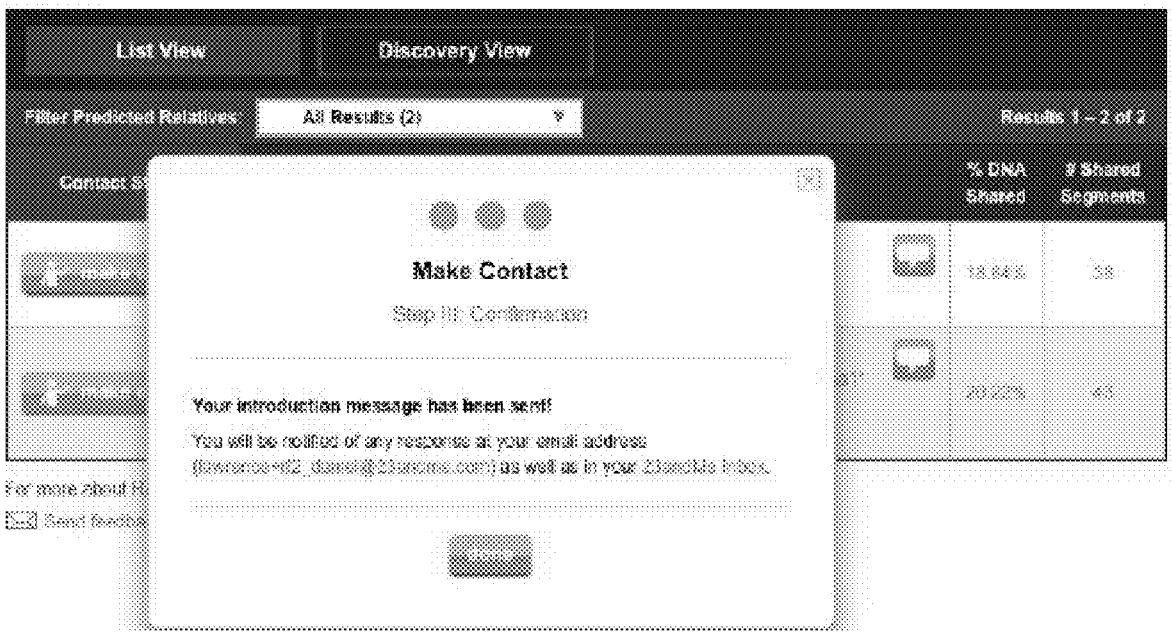

FIGS. 4E-4G show the user interface when the user selects to "make contact" with a potential relative. FIG. 4E shows the first step in making contact, where the user personalizes the introduction message and determine what information the user is willing to share with the potential relative. FIG. 4F shows an optional step in making contact, where the user is told about the cost of using the introduction service. In this case, the introduction is free. FIG. 4G shows the final step, where the introduction message is sent.

Figure 4H:

FIG. 4H shows the user interface shown to the potential relative upon receiving the introduction message. In this example, the discovery view indicates that a certain user/potential relative has requested to make a contact. The predicted relationship, personal details of the sender, and DNA sharing information are shown to the recipient. The recipient has the option to select "view message" to view the introduction message from the sender.

Figure 4I:
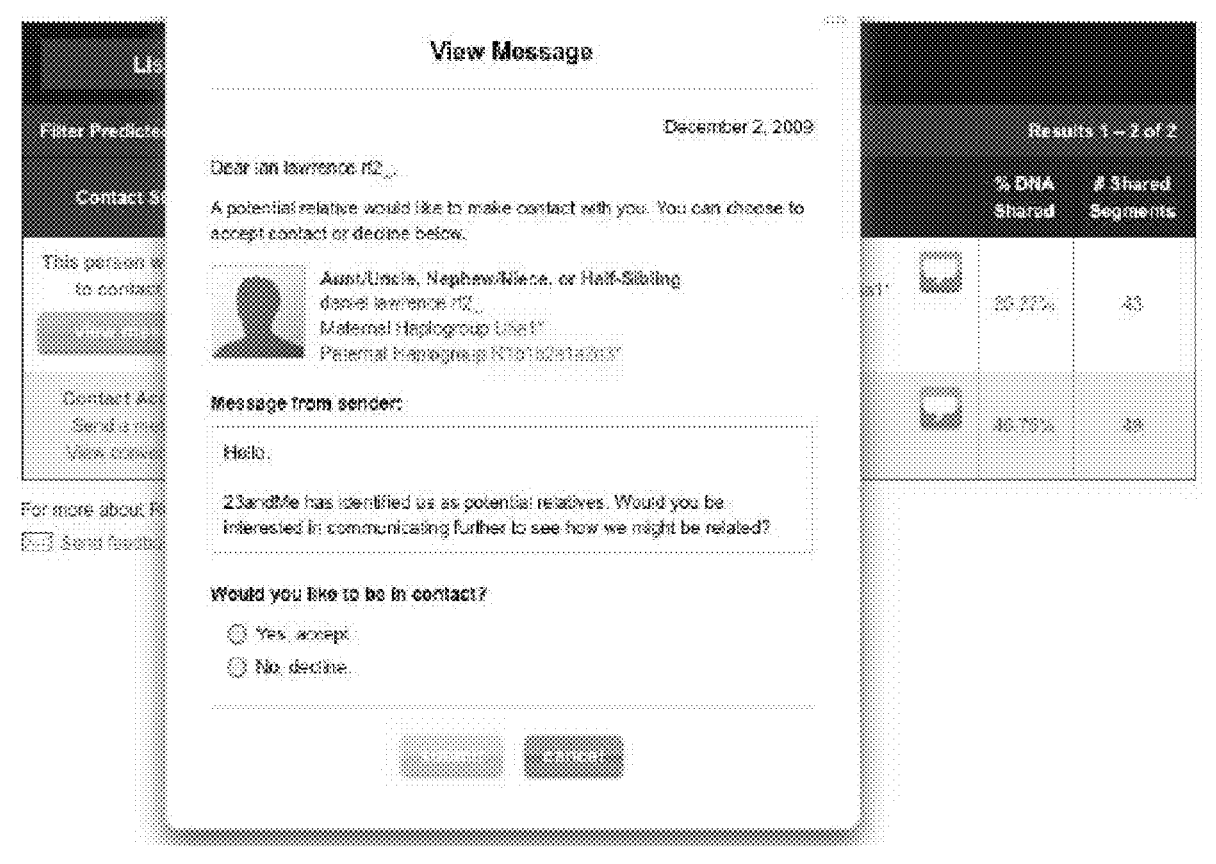

FIG. 4I shows the message as it is displayed to the recipient. In addition to the content of the message, the recipient is given the option to accept or decline the invitation to be in contact with the sender. If the recipient accepts the invitation, the recipient and the sender become connected and may view each other's information and/or interact with each other.

Many other user interfaces can be used in addition to or as alternatives of the ones shown above. For example, in some embodiments, at least some of the potential relatives are displayed in a family tree.

Determining the relationship between two users in the database is now described. In some embodiments, the determination includes comparing the DNA markers (e.g., SNPs) of two users and identifying IBD regions. The standard SNP based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g. triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

Figure 5:
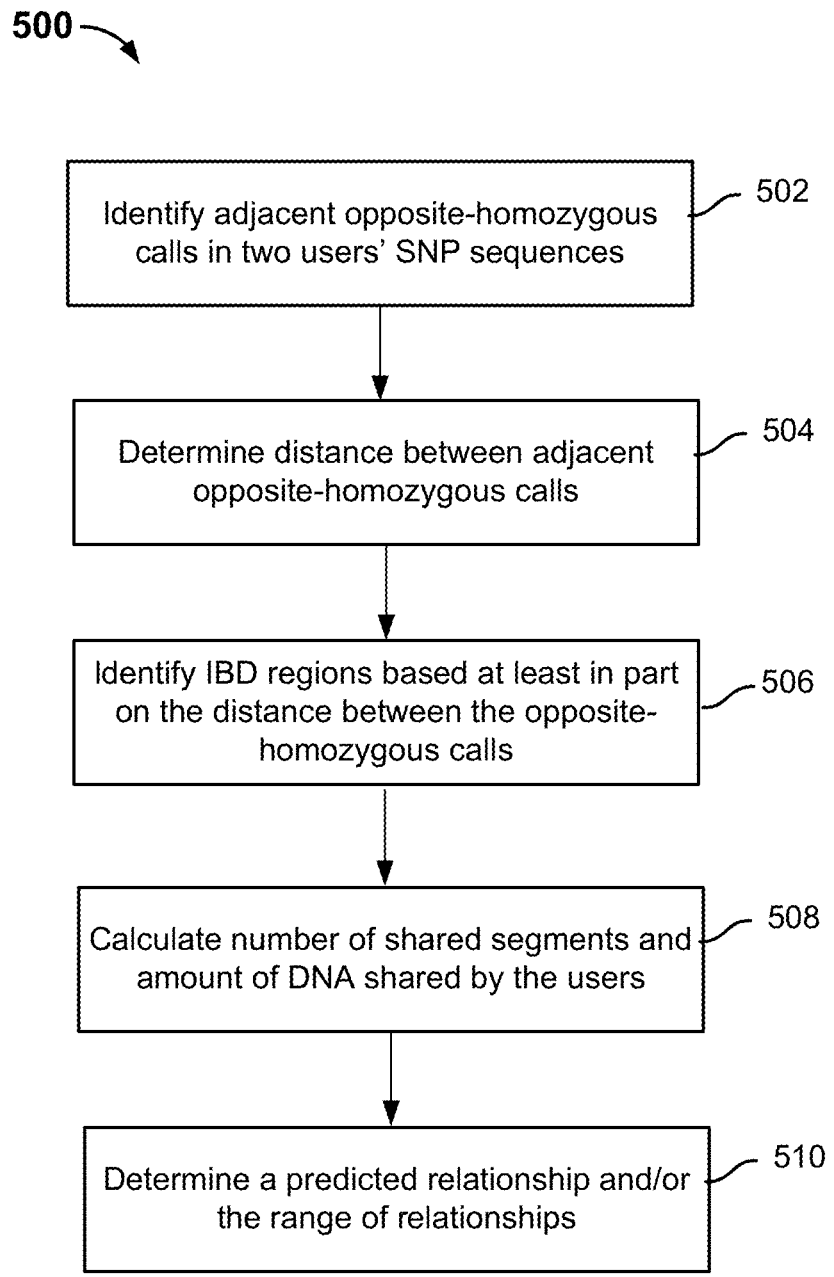
FIG. 5 is a diagram illustrating an embodiment of a process for determining the expected degree of relationship between two users.

FIG. 5 is a diagram illustrating an embodiment of a process for determining the predicted degree of relationship between two users. Process 500 may be implemented on a relative finder system such as 102 and is applicable to unphased data. At 502, consecutive opposite-homozygous calls in the users' SNPs are identified. The consecutive opposite-homozygous calls can be identified by serially comparing individual SNPs in the users' SNP sequences or in parallel using bitwise operations as described below. At 504, the distance between consecutive opposite-homozygous calls is determined. At 506, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite homozygous calls is just below the 10 cM threshold. If a large enough number of genotype calls within that interval match exactly, the interval is deemed IBD.

Figure 6:
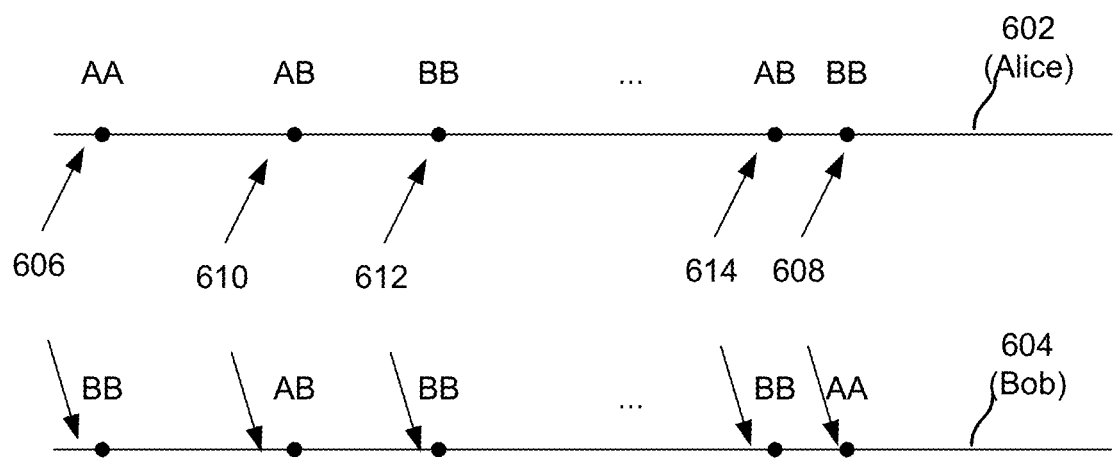
FIG. 6 is a diagram illustrating example DNA data used for IBD identification by process 500.

FIG. 6 is a diagram illustrating example DNA data used for IBD identification by process 500. 602 and 604 correspond to the SNP sequences of Alice and Bob, respectively. At location 606, the alleles of Alice and Bob are opposite-homozygotes, suggesting that the SNP at this location resides in a non-IBD region. Similarly, at location 608, the opposite-homozygotes suggest a non-IBD region. At location 610, however, both pairs of alleles are heterozygotes, suggesting that there is potential for IBD. Similarly, there is potential for IBD at location 612, where both pairs of alleles are identical homozygotes, and at location 614, where Alice's pair of alleles is heterozygous and Bob's is homozygous. If there is no other opposite-homozygote between 606 and 608 and there are a large number of compatible calls between the two locations, it is then likely that the region between 606 and 608 is an IBD region.

Returning to FIG. 5, at 508, the number of shared IBD segments and the amount of DNA shared by the two users are computed based on the IBD. In some embodiments, the longest IBD segment is also determined. In some embodiments, the amount of DNA shared includes the sum of the lengths of IBD regions and/or percentage of DNA shared. The sum is referred to as $IBD_{half}$ or half IBD because the individuals share DNA identical by descent for at least one of the homologous chromosomes. At 510, the predicted relationship between the users, the range of possible relationships, or both, is determined using the $IBD_{half}$ and number of segments, based on the distribution pattern of $IBD_{half}$ and shared segments for different types of relationships. For example, in a first degree parent/child relationship, the individuals have $IBD_{half}$ that is 100% the total length of all the autosomal chromosomes and 22 shared autosomal chromosome segments; in a second degree grandparent/grandchild relationship, the individuals have $IBD_{half}$ that is approximately half the total length of all the autosomal chromosomes and many more shared segments; in each subsequent degree of relationship, the percentage of $IBD_{half}$ of the total length is about 50% of the previous degree. Also, for more distant relationships, in each subsequent degree of relationship, the number of shared segments is approximately half of the previous number.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

Figure 7:
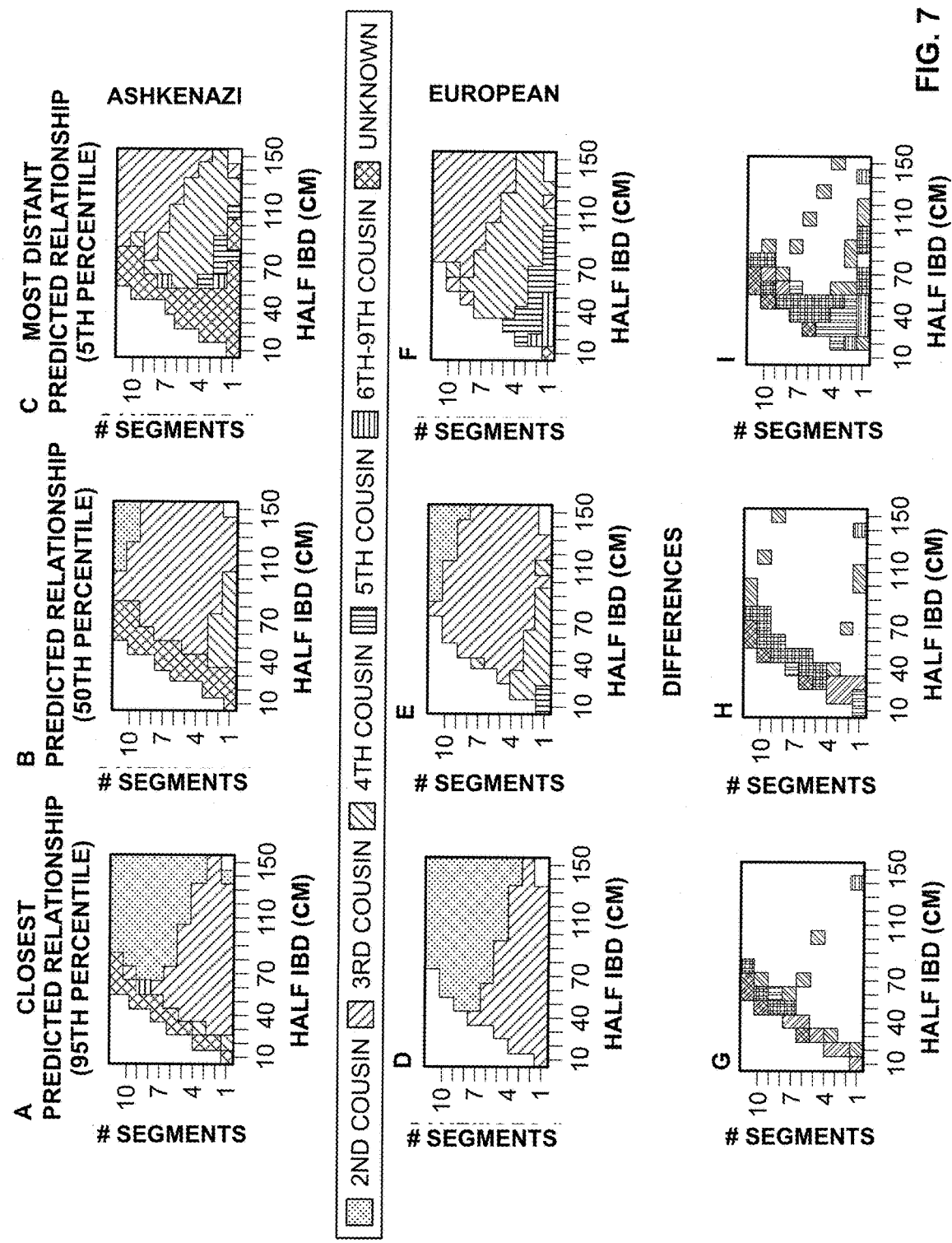
FIG. 7 is a diagram illustrating example simulated relationship distribution patterns for different population groups according to one embodiment.

There is a statistical range of possible relationships for the same $IBD_{half}$ and shared segment number. In some embodiments, the distribution patterns are determined empirically based on survey of real populations. Different population groups may exhibit different distribution patterns. For example, the level of homozygosity within endogamous populations is found to be higher than in populations receiving gene flow from other groups. In some embodiments, the bounds of particular relationships are estimated using simulations of IBD using generated family trees. Based at least in part on the distribution patterns, the $IBD_{half}$ and shared number of segments, the degree of relationship between two individuals can be estimated. FIG. 7 is a diagram illustrating example simulated relationship distribution patterns for different population groups according to one embodiment. In particular, Ashkenazi Jews and Europeans are two population groups surveyed. In panels A-C, for each combination of $IBD_{half}$ and the number of IBD segments in an Ashkenazi sample group, the 95%, 50% and 5% of obtained nth degree cousinships from 1 million simulated pedigrees are plotted. In panels D-F, for each combination of $IBD_{half}$ and the number of IBD segments in a European sample group, the 95%, 50% and 5% of obtained nth degree cousinships from 1 million simulated pedigrees are plotted. In panels G-I, the differences between Ashkenazi and European distant cousinship for the prior panels are represented. Each nth cousinship category is scaled by the expected number of nth degree cousins given a model of population growth. Simulations are conducted by specifying an extended pedigree and creating simulated genomes for the pedigree by simulating the mating of individuals drawn from a pool of empirical genomes. Pairs of individuals who appear to share $IBD_{half}$ that was not inherited through the specified simulated pedigree are marked as "unknown" in panels A-F. Thus, special distribution patterns can be used to find relatives of users who have indicated that they belong to certain distinctive population groups such as the Ashkenazi.

The amount of IBD sharing is used in some embodiments to identify different population groups. For example, for a given degree of relationship, since Ashkenazi tend to have much more IBD sharing than non-Ashkenazi Europeans, users may be classified as either Ashkenazi or non-Ashkenazi Europeans based on the number and pattern of IBD matches.

In some embodiments, instead of, or in addition to, determining the relationship based on the overall number of IBD segments and percent DNA shared, individual chromosomes are examined to determine the relationship. For example, X chromosome information is received in some embodiments in addition to the autosomal chromosomes. The X chromosomes of the users are also processed to identify IBD. Since one of the X chromosomes in a female user is passed on from her father without recombination, the female inherits one X chromosome from her maternal grandmother and another one from her mother. Thus, the X chromosome undergoes recombination at a slower rate compared to autosomal chromosomes and more distant relationships can be predicted using IBD found on the X chromosomes.

In some embodiments, analyses of mutations within IBD segments can be used to estimate ages of the IBD segments and refine estimates of relationships between users.

In some embodiments, the relationship determined is verified using non-DNA information. For example, the relationship may be checked against the users' family tree information, birth records, or other user information.

Figure 8:
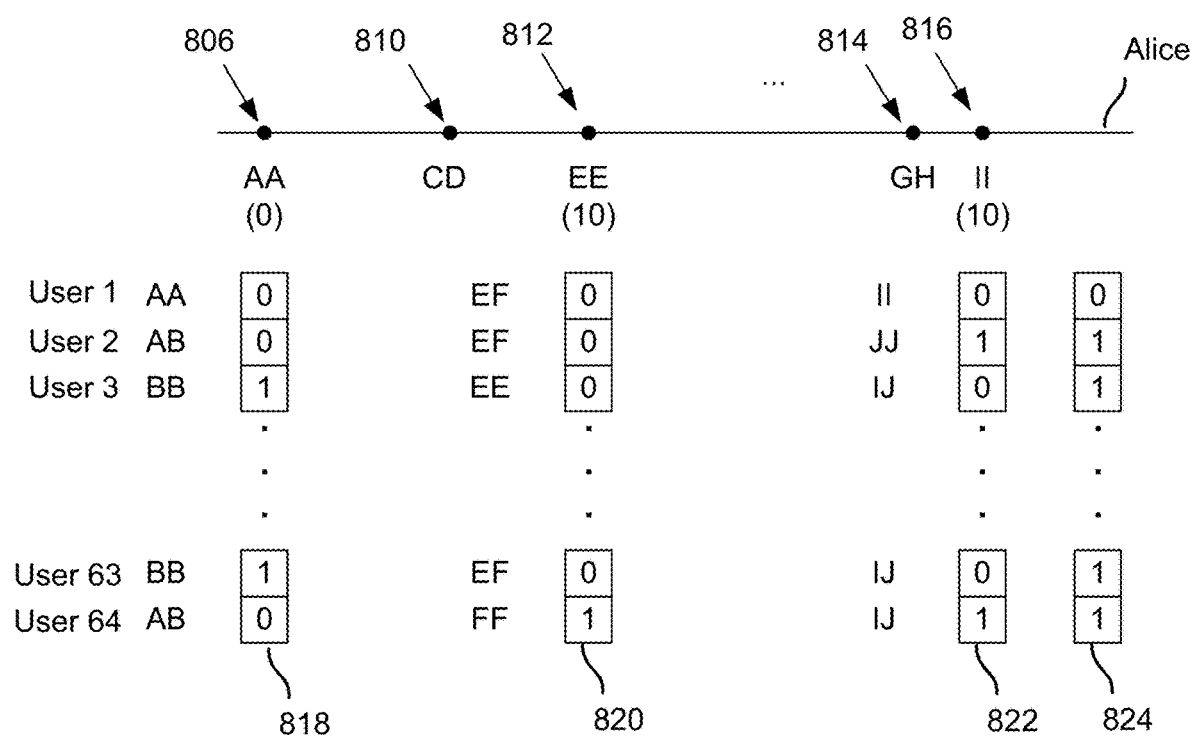
FIG. 8 is a diagram illustrating an embodiment of a highly parallel IBD identification process.

In some embodiments, the efficiency of IBD region identification is improved by comparing a user's DNA information with the DNA information of multiple other users in parallel and using bitwise operations. FIG. 8 is a diagram illustrating an embodiment of a highly parallel IBD identification process. Alice's SNP calls are compared with those of multiple other users. Alice's SNP calls are pre-processed to identify ones that are homozygous. Alice's heterozygous calls are not further processed since they always indicate that there is possibility of IBD with another user. For each SNP call in Alice's genome that is homozygous, the zygosity states in the corresponding SNP calls in the other users are encoded. In this example, compatible calls (e.g., heterozygous calls and same homozygous calls) are encoded as 0 and opposite-homozygous calls are encoded as 1. For example, for homozygous SNP call AA at location 806, opposite-homozygous calls BB are encoded as 1 and compatible calls (AA and AB) are encoded as 0; for homozygous SNP call EE at location 812, opposite-homozygous calls FF are encoded as 1 and compatible calls (EE and EF) are encoded as 0, etc. The encoded representations are stored in arrays such as 818, 820, and 824. In some embodiments, the length of the array is the same as the word length of the processor to achieve greater processing efficiency. For example, in a 64-bit processing system, the array length is set to 64 and the zygosity of 64 users' SNP calls are encoded and stored in the array.

A bitwise operation is performed on the encoded arrays to determine whether a section of DNA such as the section between locations 806 and 810 includes opposite-homozygous calls. In this example, a bitwise OR operation is performed to generate a result array 824. Any user with no opposite-homozygous calls between beginning location 806 and ending location 816 results in an entry value of 0 in array 824. The corresponding DNA segment, therefore, is deemed as an IBD region for such user and Alice. In contrast, users with opposite-homozygotes result in corresponding entry values of 1 in array 824 and they are deemed not to share IBD with Alice in this region. In the example shown, user 1 shares IBD with Alice while other users do not.

In some embodiments, phased data is used instead of unphased data. These data can come directly from assays that produce phased data, or from statistical processing of unphased data. IBD regions are determined by matching the SNP sequences between users. In some embodiments, sequences of SNPs are stored in dictionaries using a hash-table data structure for the ease of comparison. FIG. 9 is a diagram illustrating an example in which phased data are compared to identify IBD. The sequences are split along pre-defined intervals into non-overlapping words. Other embodiments may use overlapping words. Although a preset length of 3 is used for purposes of illustration in the example shown, many implementations may use words of longer lengths (e.g. 100). Also, the length does not have to be the same for every location. In FIG. 9, in Alice's chromosome pair 1, chromosome 902 is represented by words AGT, CTG, CAA, . . . and chromosome 904 is represented by CGA, CAG, TCA, . . . . At each location, the words are stored in a hash table that includes information about a plurality of users to enable constant retrieval of which users carry matching haplotypes. Similar hash tables are constructed for other sequences starting at other locations. To determine whether Bob's chromosome pair 1 shares any IBD with Alice's, Bob's sequences are processed into words at the same locations as Alice's. Thus, Bob's chromosome 906 yields CAT, GAC, CCG, . . . and chromosome 908 yields AAT, CTG, CAA, . . . . Every word from Bob's chromosomes is then looked up in the corresponding hash table to check whether any other users have the same word at that location in their genomes. In the example shown, the second and third words of chromosome 908 match second and third words of Alice's chromosome 902. This indicates that SNP sequence CTGCAA is present in both chromosomes and suggests the possibility of IBD sharing. If enough matching words are present in close proximity to each other, the region would be deemed IBD.

In some embodiments, relative relationships found using the techniques described above are used to infer characteristics about the users that are related to each other. In some embodiments, the inferred characteristic is based on non-genetic information pertaining to the related users. For example, if a user is found to have a number of relatives that belong to a particular population group, then an inference is made that the user may also belong to the same population group. In some embodiments, genetic information is used to infer characteristics, in particular characteristics specific to shared IBD segments of the related users. Assume, for example, that Alice has sequenced her entire genome but her relatives in the system have only genotyped SNP data. If Alice's genome sequence indicates that she may have inherited a disease gene, then, with Alice's permission, Alice's relatives who have shared IBD with Alice in the same region that includes the disease gene may be notified that they are at risk for the same disease.

Figure 10:
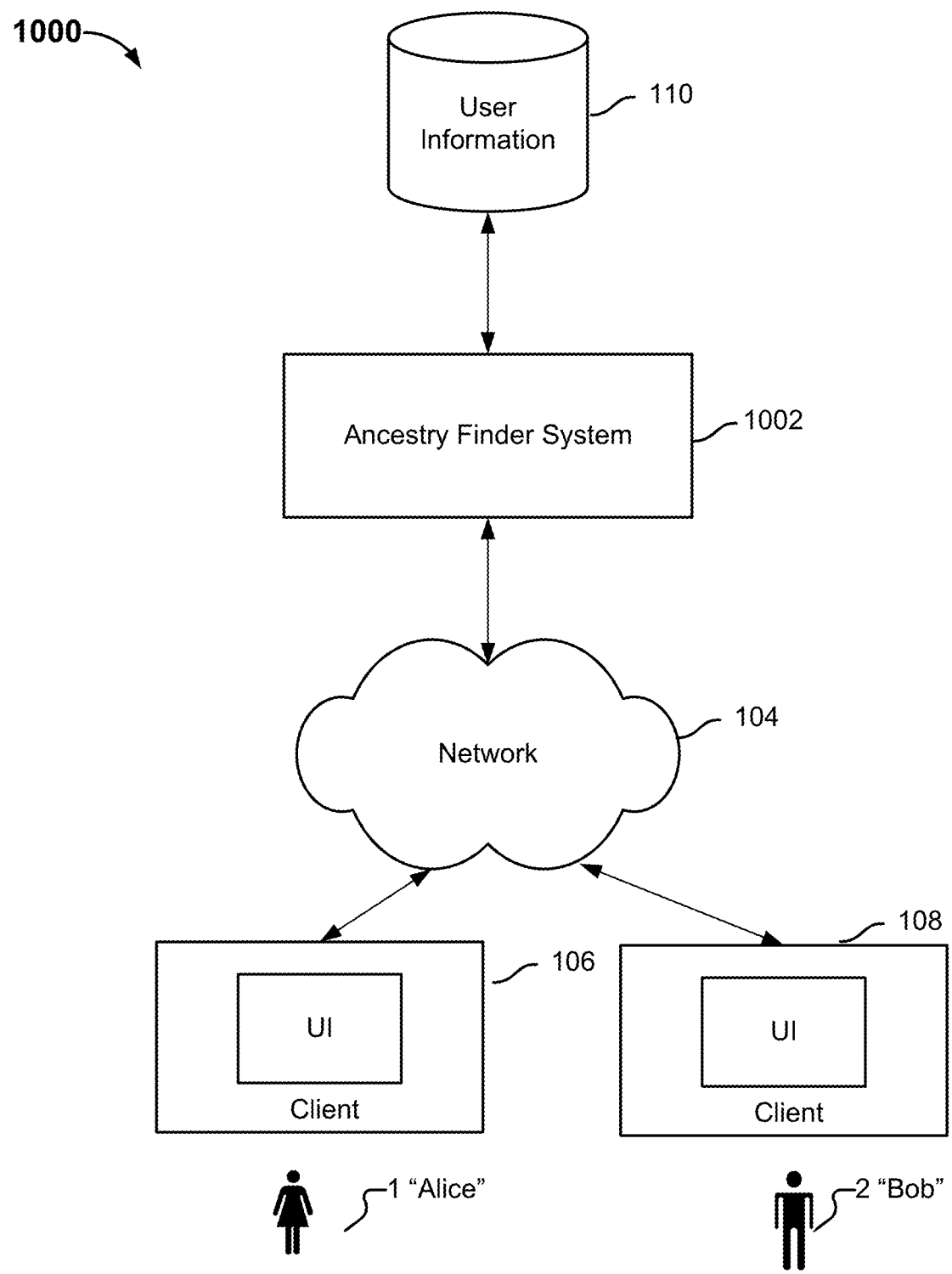
FIG. 10 is a block diagram illustrating an embodiment of an ancestry finder system.

FIG. 10 is a block diagram illustrating an embodiment of an ancestry finder system. In this example, ancestry finder system 102 may be implemented using one or more server computers having one or more processors, one or more special purpose computing appliances, or any other appropriate hardware, software, or combinations thereof. The operations of the ancestry finder system are described in greater detail below. In this example, various users of the system (e.g., user 1 ("Alice") and user 2 ("Bob")) access the ancestry finder system via a network 104 using client devices such as 106 and 108. User information (including genetic information and optionally other personal information such as family information, population group, etc.) pertaining to the users is stored in a database 110, which can be implemented on an integral storage component of the ancestry finder system, an attached storage device, a separate storage device accessible by the ancestry finder system, or a combination thereof. Many different arrangements of the physical components are possible in various embodiments. In some embodiments, the entire genome sequences or assayed DNA markers (SNPs, STRs, CNVs, etc.) are stored in the database to facilitate the relative finding process. For example, approximately 650,000 SNPs per individual's genome are assayed and stored in the database in some implementations.

System 1000 shown in this example includes genetic and other additional non-genetic information for many users. By comparing the recombining DNA information to identify shared IBD regions between various users, the ancestry finder system can infer ancestry information or other characteristics of a user.

In some embodiments, database 110 includes results of a survey of users. For example, the survey may be an ancestry survey that requests information such as the place (e.g., country and city) of birth, race, and ethnicity of the user. In some embodiments, the survey also requests information regarding relatives of the user, such as the place of birth and race/ethnicity of each of the user's parents and grandparents (if known to the user). For example, Alice may provide her place of birth and ethnicity, as well as the places of birth and ethnicities of each of her parents and grandparents. Such information may be useful for determining information about the ancestry of other users who are related to Alice and/or have a common IBD segment with Alice, as further described below. In some embodiments, Alice may also provide ancestry information for her direct maternal line (mother's mother's mother's . . . mother) as far back as possible. Alice's brother (or any male) might provide ancestry information for his direct paternal line (father's father's father's . . . father) as far back as possible. In various embodiments, the user survey results are stored separately from database 110, such as in a separate database. In various embodiments, relative finder system 102 and ancestry finder system 1002 are part of the same system and may share data.

Figure 11:
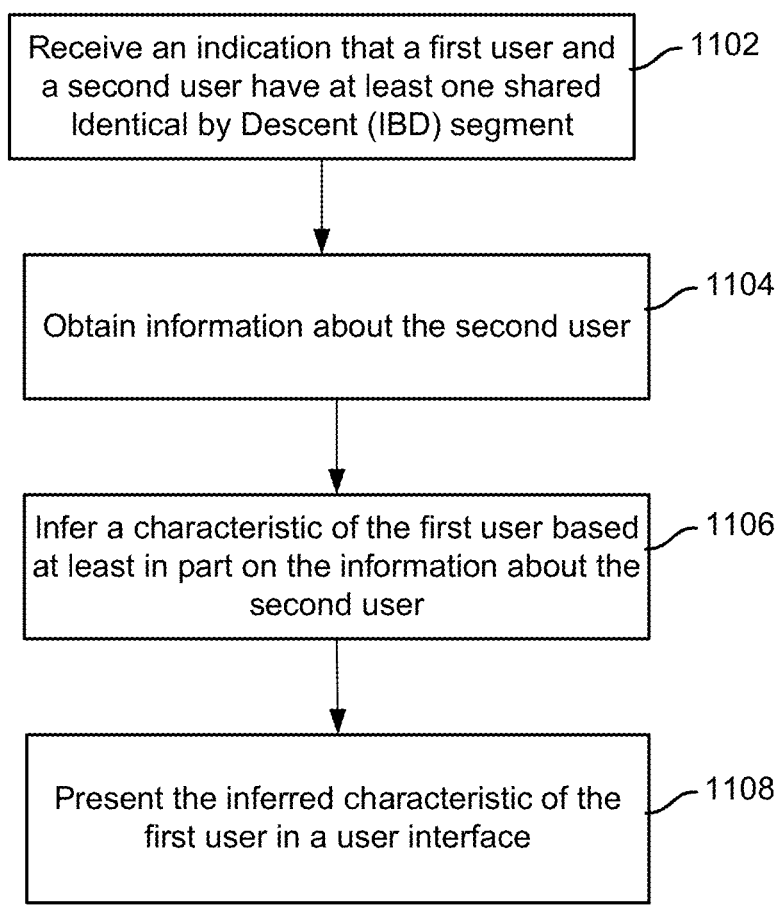
FIG. 11 is a flowchart illustrating an embodiment of a process for inferring a characteristic of an individual.

FIG. 11 is a flowchart illustrating an embodiment of a process for inferring a characteristic of an individual. Process 1100 may be implemented on an ancestry finder system such as 1100. In some embodiments, if a user has a chromosomal segment that is associated with a particular population group (e.g., based on other users having that chromosomal segment who have identified themselves as being associated with the population group), this process infers that the user has ancestry associated with that population group. The process may be invoked, for example, at a user's request to look for ancestry information and/or potential relatives this user may have in the database. One or more steps of process 1100 may be part of a batch process used to obtain ancestry information (or information used to infer ancestry information) for a plurality of users.

At 1102, an indication that a first user (e.g., Alice) and a second user (e.g., Bob) have at least one shared IBD segment is received. In some embodiments, it is determined that the first user and the second user have at least one shared IBD segment based on information retrieved from a database that stores recombining DNA information of a plurality of users as well as additional user information. For purposes of illustration, SNP information is described extensively in this and following examples. Other DNA information such as STR information, CNV information, exomic sequence information, and/or full sequence information may be used in other embodiments. In some embodiments, the second user is an individual from a reference database, and not necessarily a user of the ancestry finder system.

At 1104, information about the second user is obtained. In some embodiments, the information about the second user comprises one or more characteristics of one or more relatives of the second user. In some embodiments, at least one characteristic is ancestry information. For example, the information about the second user could comprise ancestry information about the four grandparents of the second user, such as the birthplaces of the four grandparents. Such information could, for example, have been provided by the second user when filling out a survey of characteristics of the user and the user's relatives, such as an ancestry survey, an example of which was previously described. In other embodiments, such information could be provided by a reference database. In some embodiments, the information about the second user is obtained from a database, such as database 110.

At 1106, a characteristic of the first user is inferred based at least in part on the information about the second user. If the first user and second user share at least one common IBD segment, information about the first user could be inferred from known information about the second user. For example, if it is known that the second user's four grandparents were all born in Ireland, than it can be inferred that the first user has at least some Irish ancestry, or at least that there is someone of Irish ancestry associated with that segment value. Characteristics can include ancestry information. Other examples of characteristics that can be inferred besides ancestry information include any other inherited characteristic, such as information associated with diseases, traits, or any other form of phenotypic information.

At 1108, the inferred characteristic of the first user is presented in a user interface. Various examples of user interfaces for presenting, displaying, or notifying of the inferred characteristic are possible. Some examples of user interfaces include a table view, an (extended) discovery view, a karyotype view, a geographical map view, as more fully described below. For example, a discovery view may display a list or table of users that are found to be related to the user based on the relative finder system. In addition to displaying relative finder results, ancestry information is displayed next to each relative. For example, next to each relative, there may be a column for each grandparent of that relative. An indication of ancestry information for each grandparent may be displayed in each column, as more fully illustrated below. Other examples of user interfaces include a family tree, which displays a family tree filled with inferred ancestry information about each relative. In some embodiments, the system actively notifies the users by sending messages or alerts about ancestry information when it becomes available or at a given interval.

In some embodiments, it is determined that for a particular segment, the first user shares IBD with other users besides the second user. If the other users that share this chromosomal segment have conflicting inferred ancestry (or other characteristic) information, then this conflict may be handled in various ways in various embodiments. In some embodiments, all the information is presented. In some embodiments, the information is processed to infer ancestry (or other characteristic information). For example, the information may be processed using a majority rules technique. For example, if the ancestry associated with the majority of the matching users is German, then it is inferred that that segment is associated with German ancestry. In some embodiments, for each segment and each possible value of each segment, the information is processed (e.g., using majority rules), and the processed result is pre-computed and stored for future reference by any of the matching users.

In some embodiments, 1102 is part of a batch process in which a plurality of users (e.g., from a database) are pre-processed to determine shared IBD segments. The results comprise shared IBD segments for a plurality of users. For example, for a particular user, there may be 278 matches to various segments of the user's chromosomes. At 1104, these results are cross-referenced with a database of information (e.g., ancestry information) about those matching users. For example, of the 278 matches, 49 of those users have completed an ancestry information survey that can be used to infer ancestry information about the particular user.

Figure 12:
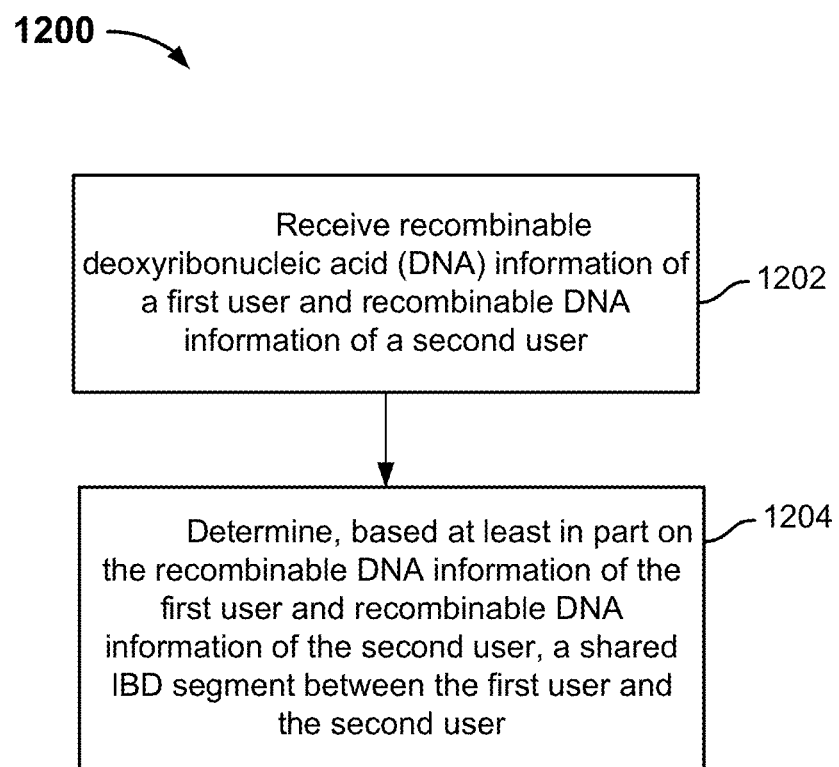
FIG. 12 is a flowchart illustrating an embodiment of a process for determining that a first user and a second user share at least one IBD segment.

FIG. 12 is a flowchart illustrating an embodiment of a process for determining that a first user and a second user share at least one IBD segment. Process 1200 may be implemented on an ancestry finder system such as 1100. The process may be performed, for example, at 1102 of process 1100. At 1202, recombining DNA information of a first user and recombining DNA information of a second user are received. At 1204, a shared IBD segment between the first user and the second user is determined based at least in part on the recombining DNA information of the first user and recombining DNA information of the second user. Any appropriate technique may be used to determine the shared IBD segment. For example, in some embodiments, one or more steps of process 500 are used to determine the shared IBD segment. In some embodiments, one or more steps of the process described with respect to FIG. 6, 8, or 9 is used to determine the shared IBD segment.

FIG. 13 shows an interface example for a table view of an ancestry finder system. In some embodiments, this interface is used to present inferred ancestry information for a user at 1108. In this example, a table is displayed or presented that illustrates the results a typical user of European ancestry might receive. Each row in the table corresponds to a chromosomal segment that the user shares by IBD with another individual (i.e., a relative finder hit). Three of the segments are to (one or more) individuals of Irish ancestry, and one is to an individual of German ancestry. This table shows a relatively low number of ancestry finder hits. In other words, only about 40 cM (roughtly 40 Mb), or a bit more than half a percent of this user's genome. (The calculation is 40 cM/6000 cM=0.7%. The denominator is not 3000 cM, the length of the diploid genome, but twice that, the length of the haploid genome, because there could be an ancestry finder hit to either chromosome. This typically is the case with Ashkenazim.) How much of the genome is covered depends on the number of individuals in the database from the same subpopulations as the user and the consanguinity of that subpopulation. A hit or match means that at least a portion of the user's genome was found in the indicated part of the world prior to the era of intercontinental travel.

In various embodiments, other types of interfaces, tables, charts, or views may be used. For example, a table of the top ten countries associated with the user's ancestral origin may be presented or displayed. These top ten countries are determined based on the total number of non-overlapping DNA segments attributable to each country. A pie chart may be used to show the breakdown among countries.

Figure 14:
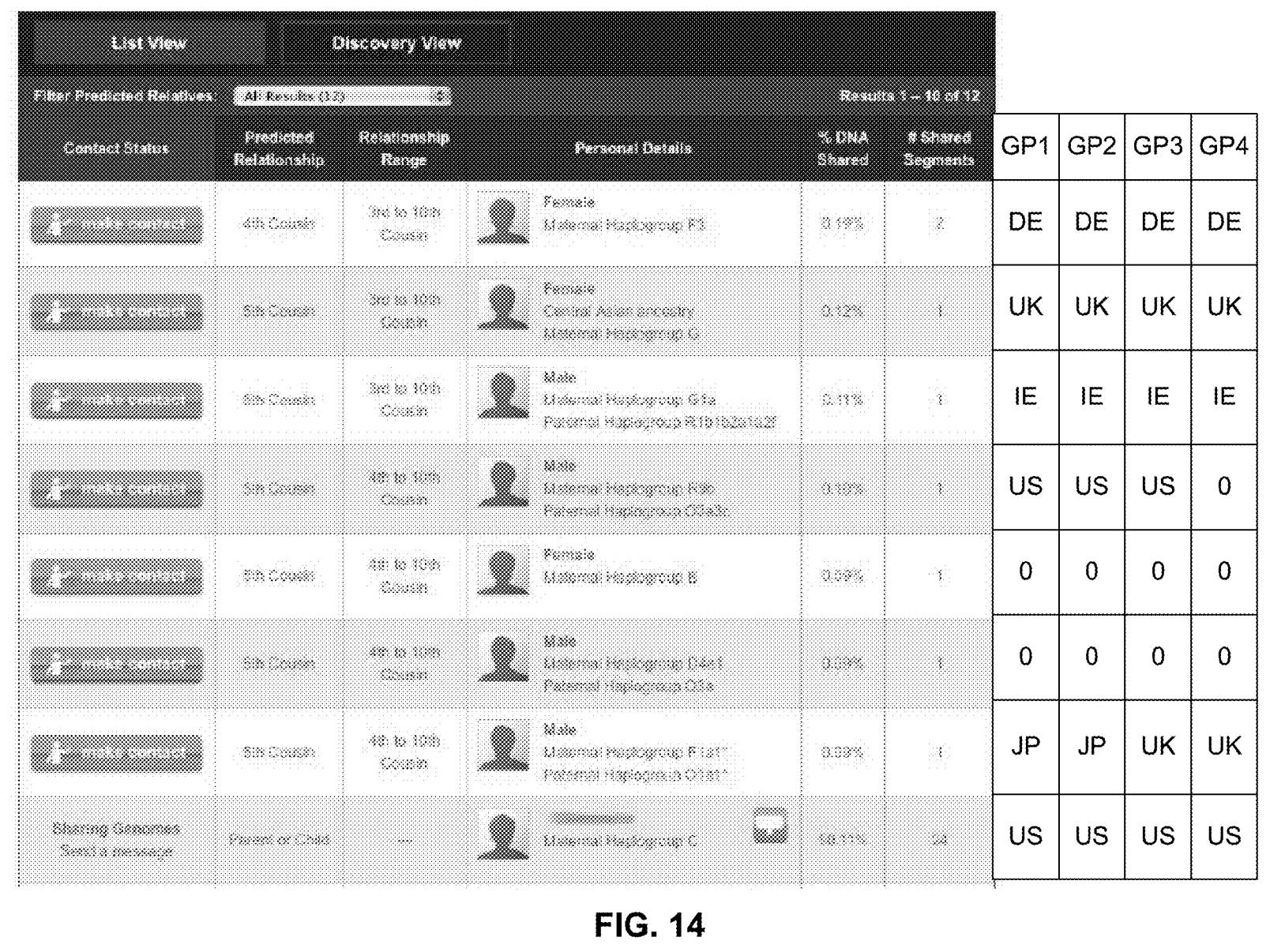
Figure 15:
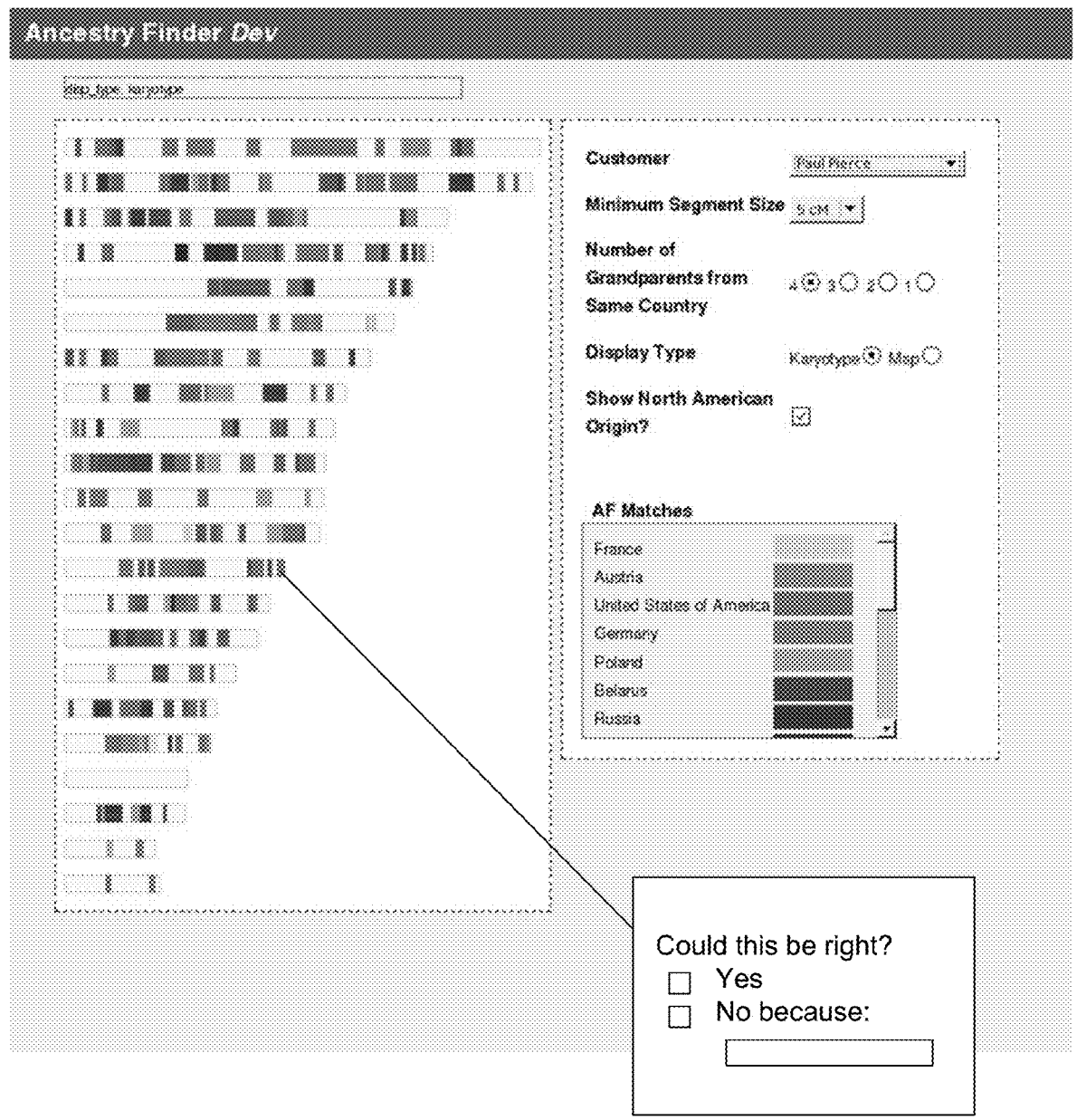
FIG. 15 shows an interface example for a karyotype view of an ancestry finder system.

FIG. 14 shows an interface example for the discovery view of a relative finder system that incorporates an ancestry finder system. In some embodiments, this interface is used to present inferred ancestry information for a user at 1108. In this example, the user interface of FIG. 4C is shown in addition to four new columns: GP1-GP4, representing Grandparents 1-4. For each relative, ancestry information is shown in each of the columns for that relative. In this example, the ancestry information is represented by codes that indicate birth countries of the grandparents. DE is Germany, UK is the United Kingdom, IE is Ireland, US is the United States, and JP is Japan. For example, the first row shows a $4^{th}$ cousin with four grandparents who are all of German ancestry. In other embodiments, other ancestry information could be displayed, such as race/ethnicity (e.g., NA for Native American). In various embodiments, various other ancestry information could be provided, such as information about the relative's parents or siblings. In various embodiments, various other information about characteristics of the relative could be provided, including disease, trait, or any other form of phenotypic information FIG. 15 shows an interface example for a karyotype view of an ancestry finder system. In some embodiments, this interface is used to present inferred ancestry information for a user "Paul Pierce" at 1108.

In this example, the user interface shows a graphic of a user's chromosome on the left hand side. On each chromosome, various segments are colored based on with which ancestry (France, Austria, United States, etc.) that segment is associated. In some embodiments, a segment is associated with an ancestry based on an IBD match with an individual of known ancestry. For example, if a user's segment has an IBD match with another individual, and the birth country of all four grandparents of that individual is provided or known, then it can be inferred that the user's segment is associated with that birth country. In other words, that shared IBD segment was associated with that part of the world (prior to the era of intercontinental travel).

On the right hand side, a control panel is shown. In the control panel, the customer (user) name is shown, along with user configurable settings. "Minimum segment size" is the minimum length of a matching IBD segment, in this example, 5 cM. Minimum segment size governs the minimum length of displayed ancestry finder hits. It's given in centiMorgans (cM) in the example shown, but can also be expressed in terms of base pairs, kilobases, megabases, or any other appropriate unit. In this example, most hits are short, so increasing the minimum quickly reduces the number of segments displayed. These longer hits, although fewer, are increasingly likely to indicate recent shared ancestry, and therefore to represent genuine/applicable ancestry finder results. In this example, the great majority of IBD hits, and thus ancestry finder segments, are between 5 cM and 10 cM in length. The lower end is controlled by a few threshold parameters in the IBD matching technique and can take any appropriate value. The lower edge might be different for the IBD hits on live. One range might be 5 cm to 20 cM (20 cM is the approximate length of chromosome 22). Although a pull down menu is shown, in various embodiments, a slider or other element could be used, with a default initial value.

"Number of grandparents from the same country" indicates the minimum number of grandparents from the same country in order for an association to be made, as will be more fully described below. In this example, ancestry associations for a segment are only made if the birth countries of all four grandparents are the same. "Display type" indicates that this is a karyotype display.

"Show North American origin?" indicates whether to include the United States and Canada as ancestry finder matches. For example, a user may desire to exclude North American origin matches because they may not be as informative since most individuals born in North America have ancestry in other parts of the world. In some cases, if this option is unchecked, then relatively fewer number of hits will result because there are many users whose four grandparents are from the United States or Canada. This is a toggle in the example, but other user interface elements may be used.

In some embodiments, a dialog box such as the one shown may be used for a user to provide feedback in this view or any other view (such as the discovery view). For example, the dialog box may open when a cursor hovers over one of the segments. The shown dialog box asks the user whether the indicated ancestry information could be right. The user can indicate "Yes" or "No" and provide a reason. In some embodiments, this feedback is used by the ancestry finder system to improve future inferences. For example, a user may see one segment that is colored brown to indicate Japan. If the user knows that he does not have any Japanese ancestry, he may select "No" in the dialog box. This may happen, for example, if the individual with the matching IBD segment to the user has indicated his grandparents are all from Japan due to misinformation. This could also happen if there is misleading information. For example a user could be born in Australia, but not be Aborigines. In some cases, a particular IBD segment may be found in more than one part of the world, leading to this result. For example, there may be tracks of chromosome that do not actually correspond to recent shared ancestry—they could correspond to old ancestry and be shared by many users.

In various embodiments, other user configurable settings may be included, such as an option to Show Public Reference Individuals and/or Show Relative Finder Users. There may be hits to customers via the ancestry survey, and to anonymous reference individuals of known ancestry from public genotype databases. The customer may wish to toggle visibility of the public individuals/Relative Finder. In some embodiments, this could rotate through three states: Both->Relative Finder Users Only->Public Only.

An option to "Notify Me of Changes to My Ancestry Finder Results" may be provided. Ancestry finder results will change/improve with time. This would allow a user to indicate whether and how the user wishes to be notified of these changes. For example, the user could request to be notified as soon as they happen (up to daily), weekly in a batch, monthly in a batch. The user could indicate which results the user wants to be notified of (e.g., four grandparents, three grandparents, and/or Non-North American).

FIG. 16 shows an example of the effect of varying some of the settings in a karyotype view of an ancestry finder system, such as that shown in FIG. 15.

"Number of Grandparents from Same Country" is the minimum number of co-located grandparents for an ancestry finder match to be made. This governs how many grandparents of the individual matching a user must be associated with the same country/ethnicity. For example, if four, then only segments for which all four grandparents come from the same country will be shown. The table shows the overall distribution of ancestry survey responses across an example database of users. The possible values are integers from four to one, inclusive.

Varying "Number of Grandparents from Same Country" and "Show North American Origin?" affects the number and informativeness of ancestry finder hits displayed. For example, in an example database, most customers of European descent have about 100 relative finder hits in the database, and about a third of the users have taken an ancestry survey, this means there are 100*(⅓) or about 30 users who match and have provided ancestry information via the ancestry survey. Generally speaking, the most informative ancestry finder matches are those when there is a match who has four grandparents from the same country, and that country is not the US or Canada. Since such matches are relatively rare in the example database, perhaps 0 to 5 of the approximately 30 matches from above, users may wish to see their other matches, even though they may be less informative. Decreasing the number of grandparents required to be from the same country from 4 to 3 to 2 to 1 increases the number of hits displayed, as does allowing matches from the US and Canada to be shown.

Figure 17:
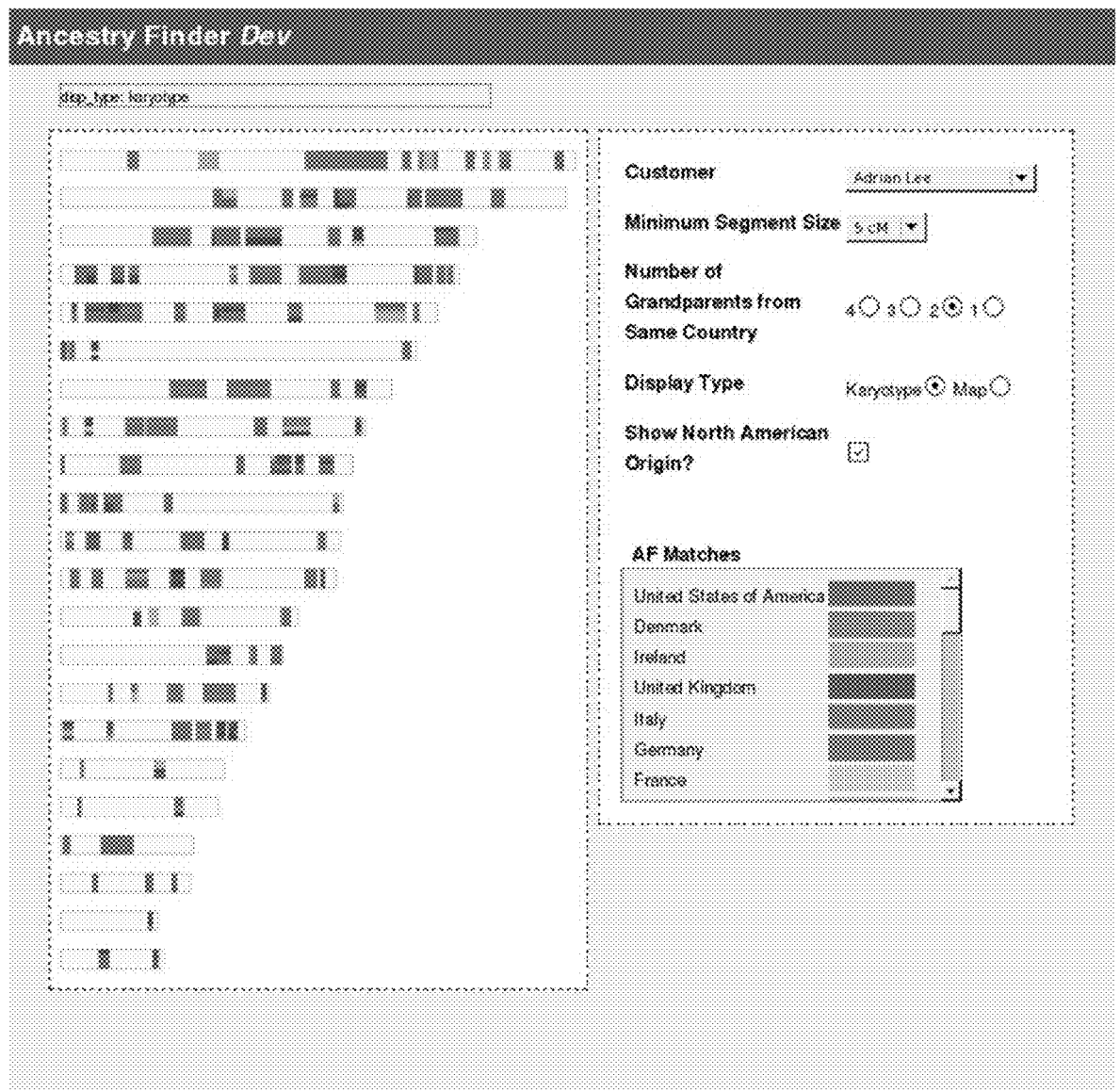
FIG. 17 shows an interface example of a karyotype view of an ancestry finder system in which "Number of grandparents from the same country" is 2.

FIG. 17 shows an interface example of a karyotype view of an ancestry finder system in which "Number of grandparents from the same country" is 2. In this example, the interface of FIG. 15 is shown for a user "Adrian Lee" who has selected 2 as the "Number of grandparents from the same country." This means that for each shared IBD segment shown (colored), the user had shared IBD with someone who has at least two grandparents from the same country. As shown, some of the segments show two or more colors (split horizontally) to indicate that that segment is IBD matched with someone whose grandparents could be from as many as three different countries. In contrast, FIG. 15 shows only one color per segment because all four grandparents must be from the same country. In various embodiments, a variety of graphical elements or visual cues may be used to depict such inferences about characteristics (such as ancestry information) that have been made based on one or more shared IBD segments.

Figure 18:
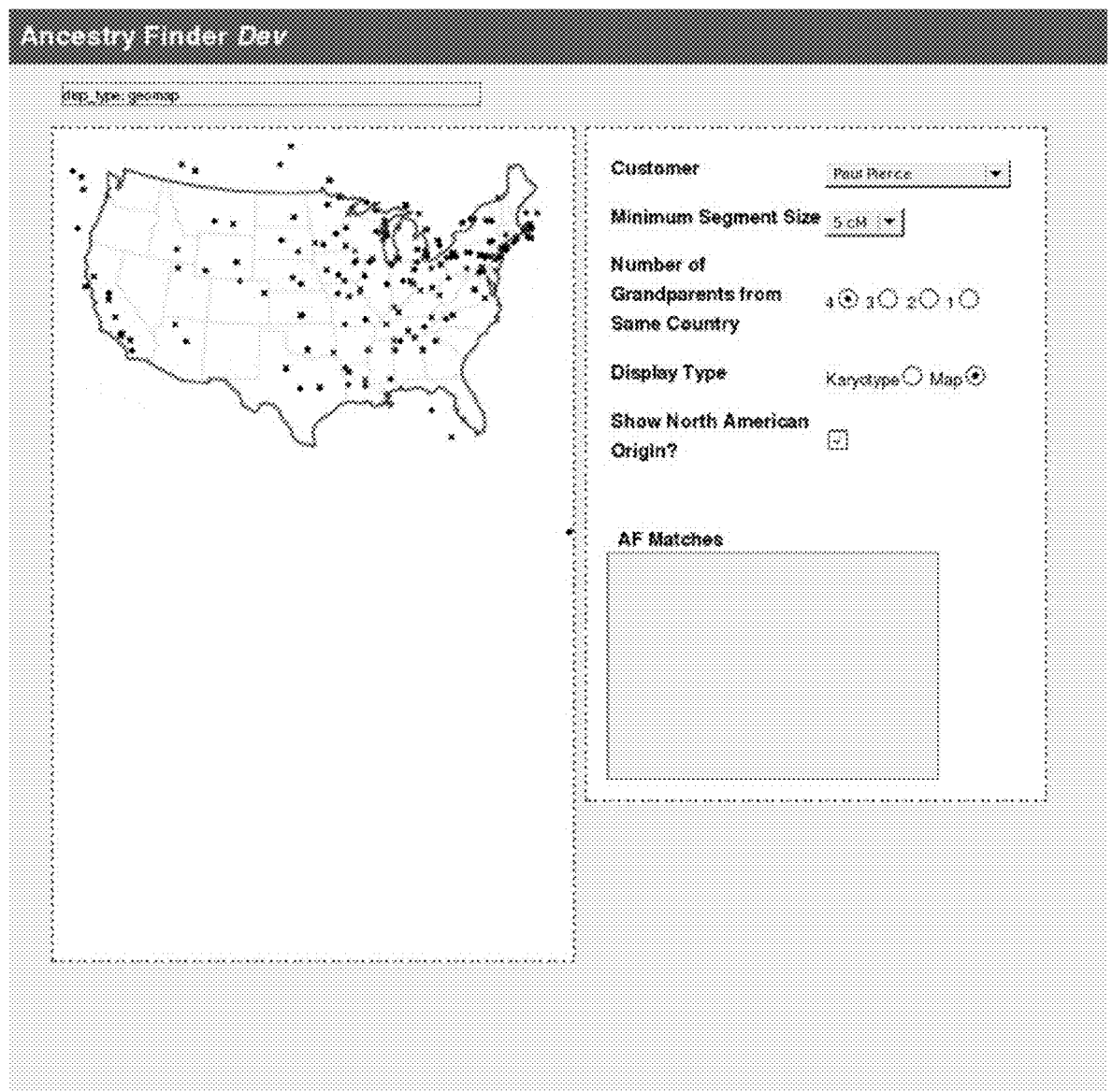
FIG. 18 shows an interface example for a geographical map view of an ancestry finder system.

FIG. 18 shows an interface example for a geographical map view of an ancestry finder system. The left hand side shows a map of some region of the world. The dots are latitude/longitude coordinates inferred from text typed in by users describing their specific places of birth, and/or those of their ancestors. The dots are the birthplaces of US-born grandparents of other users who have an IBD match with user Paul Pierce. The match is based on a minimum segment size of 5 cM, minimum number of grandparents from the same country of 4, and North American origin. For example, the map could be of North America.

Figure 19:
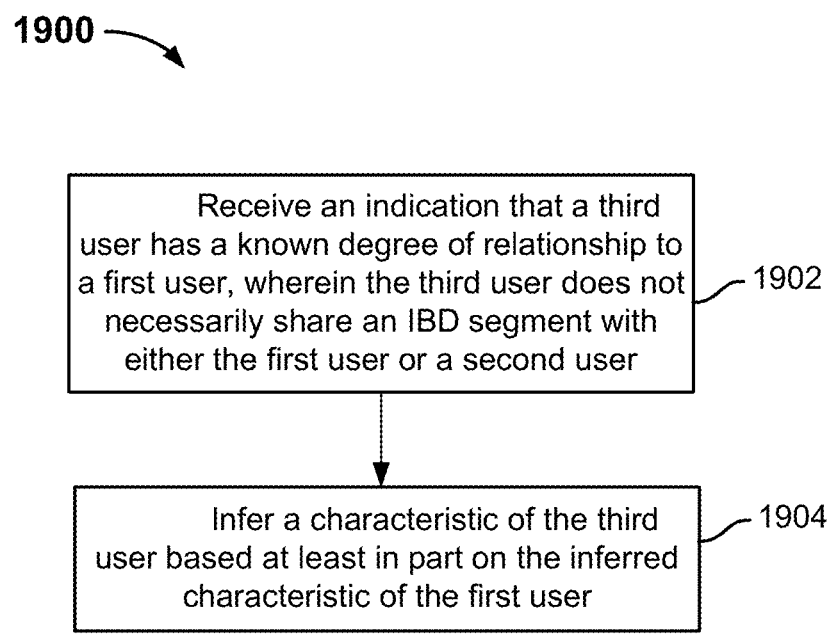
FIG. 19 is a flowchart illustrating an embodiment of a process for inferring a characteristic of an individual.

FIG. 19 is a flowchart illustrating an embodiment of a process for inferring a characteristic of an individual from the ancestry or other phenotypic information of a second individual, even if the two individuals are not related by DNA. Process 1900 may be implemented on an ancestry finder system such as 1100. The process may be invoked, for example, at a user's request to look for ancestry information. In some embodiments, this process is performed between 1106 and 1108 of process 1100, for cases in which a third user is requesting ancestry information. In this case, it is known that the third user is related to the first user, but the third user does not share an IBD segment with the second user. In some cases, the third user does not share an IBD segment with the first user either.

For example, the third user may be a sibling of the first user, but the third user does not have an IBD match with any other user in the database. However, the first user has an IBD match with the second user. Because it is known that the first user and the third user are siblings, and that the first user and second user have shared IBD for at least one segment, then, in some embodiments, ancestry information for the third user can be inferred from the ancestry information about the second user. In some cases, this means that it need not be determined whether the third user has any shared IBD segments with the second user, and this ancestry information can be inferred as soon as it is known that the third user is a sibling of the first user.

As a more specific example, the first user and the third user are full siblings, the second user is the father of the first user, the first user has a segment that is a shared IBD segment with his father (the second user), but the third user does not share that IBD segment with his father (the second user). If both of the father's parents are from Germany, then it can be inferred that the third user has at least two grandparents, his paternal grandparents, from Germany. If instead the relationship between the first user and second user is not known, perhaps because the second user is a distant cousin of the first user instead of the father, then it can at least be inferred that the third user has German ancestry, because the third user's lineages are identical to those of the first user's.

At 1902, an indication that a third user has a known degree of relationship to the first user is received. The third user does not necessarily share an IBD segment with either the first user or the second user. In the example above, the known degree of relationship between the third user and the first user is "sibling."

At 1904, a characteristic of the third user is inferred based at least in part on the inferred characteristic of the first user. In the example above, it is inferred that the third user has German ancestry, or if it is known that the second user is the father of the first user, then it is inferred that the third user has at least two grandparents from Germany.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. An ancestry finder system comprising one or more processors and one or more memories, the one or more processors being configured to:

An ancestry finder system comprising one or more processors and one or more memories, the one or more processors being configured to:
  (a) retrieve deoxyribonucleic acid (DNA) information of a first user and a plurality of other users, wherein the DNA information comprises genetic markers, and wherein each user of the plurality of other users has at least two grandparents who have a same birth country or a same ethnicity;
  (b) process in parallel the genetic markers of the first user and the plurality of other users to estimate lengths of one or more identical-by-descent (IBD) segments between the first user and each user of the plurality of other users,
  wherein:
    to process in parallel comprises to (i) perform a bitwise operation on a bit array to determine whether a segment of DNA on a pair of chromosomes includes opposite-homozygous calls between the first user and each user of the plurality of other users and (ii) estimate the lengths of the one or more IBD segments based on results of the bitwise operation on the bit array;
    the bit array has a dimension for user and a dimension for genetic marker; and
    each element of the bit array indicates whether or not a genetic marker is opposite homozygous between the first user and a user of the plurality of other users;
  (c) determine an ancestral origin of at least one chromosomal segment of the first user to be a birth country, a geographical region, or an ethnicity of at least two grandparents of a matching user who have a same birth country, a same geographical region, or a same ethnicity, wherein the first user and the matching user share the least one chromosomal segment, and wherein the at least one chromosomal segment comprises at least one IBD segment whose length is estimated as meeting a minimum length based on the results of the bitwise operation on the bit array;
  (d) cause to display in a graphical user interface ancestral information pertaining to the ancestral origin of the at least one chromosomal segment of the first user, the ancestral information comprising a graphical representation of a karyotype of the first user, wherein the karyotype of the first user comprises one or more chromosome pairs, wherein the one or more chromosome pairs comprise the at least one chromosomal segment corresponding to the at least one IBD segment whose length is estimated as meeting the minimum length based on the results of the bitwise operation on the bit array, and wherein the ancestral origin of the at least one chromosomal segment is indicated on the at least one chromosomal segment
  (e) cause to display in the graphical user interface an input element for adjusting the minimum length;
  (f) receive via the input element a user input to adjust the minimum length;
  (g) repeat (c) using the adjusted minimum length, wherein the at least one IBD segment's length is estimated as meeting the adjusted minimum length; and
  (h) cause to update in the graphical user interface the graphical representation of the karyotype of the first user, wherein the at least one chromosomal segment of the karyotype of the first user corresponds to the at least one IBD segment whose length is estimated as meeting the adjusted minimum length.

2. The system of claim 1, wherein the array comprises two or more rows corresponding to two or more users and two or more columns corresponding to two or more genetic markers.

3. The system of claim 2, wherein the two or more users comprise at least 64 users.

4. The system of claim 1, wherein the birth country, the geographical region, or the ethnicity of the at least two grandparents of the matching user are reported by the matching user.

5. The system of claim 1, wherein the ancestral origin of the at least one chromosomal segment is indicated by a graphical characteristic.

6. The system of claim 5, wherein the ancestral origin of the at least one chromosomal segment is indicated by a color.

7. The system of claim 1, wherein the ancestral origin is based on a birth country or an ethnicity of at least two grandparents of each of two or more matching users.

8. The system of claim 1, wherein the at least two grandparents comprise at least three or four grandparents.

9. The system of claim 1, wherein the ancestral origin of the at least one chromosomal segment of the first user comprises two or more different birth countries, geographical regions, or ethnicities.

10. The system of claim 1, wherein the first user and the matching user are related but previously unknown to be related.

11. The system of claim 1, wherein the minimum length of the IBD segment is provided by a user through a GUI.

12. The system of claim 1, wherein the genetic markers comprise 650,000 SNPs.

13. A method of operating an ancestry finder database with hundreds of thousands of genetic markers to display an ancestry origin of at least one chromosomal segment of a first user, comprising:
 (a) retrieving deoxyribonucleic acid (DNA) information of a first user and a plurality of other users, wherein the DNA information comprises genetic markers, and wherein each user of the plurality of other users has at least two grandparents who have a same birth country or a same ethnicity;
 (b) processing, using one or more processors of an ancestry finder system, the genetic markers of the first user and the plurality of other users to estimate lengths of one or more identical-by-descent (IBD) segments between the first user and each user of the plurality of other users;
 (c) determining, using the one or more processors, an ancestral origin of at least one chromosomal segment of the first user to be a birth country, a geographical region, or an ethnicity of at least two grandparents of a matching user who have a same birth country, a same geographical region, or a same ethnicity, wherein the first user and the matching user share the least one chromosomal segment, and wherein the at least one chromosomal segment comprises at least one IBD segment whose length is estimated as meeting a minimum length based on the estimated lengths of the one or more IBD segments;
 (d) causing to display in a graphical user interface ancestral information pertaining to the ancestral origin of the at least one chromosomal segment of the first user, the ancestral information comprising a graphical representation of a karyotype of the first user, wherein the karyotype of the first user comprises one or more chromosome pairs, wherein the one or more chromosome pairs comprise the at least one chromosomal segment corresponding to the at least one IBD segment whose length is estimated as meeting the minimum length, and wherein the ancestral origin of the at least one chromosomal segment is indicated on the at least one chromosomal segment (e) causing to display in the graphical user interface an input element for adjusting the minimum length;
 (f) receiving via the input element a user input to adjust the minimum length;
 (g) repeating (c) using the adjusted minimum length, wherein the at least one IBD segment's length is estimated as meeting the adjusted minimum length; and
 (h) causing to update in the graphical user interface the graphical representation of the karyotype of the first user, wherein the at least one chromosomal segment of the karyotype of the first user corresponds to the at least one IBD segment whose length is estimated as meeting the adjusted minimum length.

14. The method of claim 13, wherein the ancestral origin of the at least one chromosomal segment is indicated by a graphical characteristic.

15. The method of claim 13, wherein the ancestral information pertaining to the ancestral origin of the at least one chromosomal segment of the first user comprises a table of countries associated with the first user's ancestral origin.

16. The method of claim 13, wherein the ancestral information pertaining to the ancestral origin of the at least one chromosomal segment of the first user comprises a pie chart of countries associated with the first user's ancestral origin.

17. The method of claim 13, wherein the ancestral information pertaining to the ancestral origin of the at least one chromosomal segment of the first user comprises a map of countries associated with the first user's ancestral origin.

18. A computer program product, the computer program product being embodied in a tangible non-transitory computer readable storage medium and comprising computer instructions for estimating and displaying an ancestral origin of at least one chromosomal segment of a first user, the computer instructions comprising:
 (a) retrieving deoxyribonucleic acid (DNA) information of a first user and a plurality of other users, wherein the DNA information comprises genetic markers, and wherein each user of the plurality of other users has at least two grandparents who have a same birth country or a same ethnicity;
 (b) processing in parallel the genetic markers of the first user and the plurality of other users to estimate lengths of one or more identical-by-descent (IBD) segments between the first user and each user of the plurality of other users,
 wherein:
  the processing in parallel comprises (i) performing a bitwise operation on a bit array to determine whether a segment of DNA on a pair of chromosomes includes opposite-homozygous calls between the first user and each user of the plurality of other users and (ii) estimating the lengths of the one or more IBD segments based on results of the bitwise operation on the bit array;
  the bit array has a dimension for user and a dimension for genetic marker; and
  each element of the bit array indicates whether or not a genetic marker is opposite homozygous between the first user and a user of the plurality of other users;
 (c) determining an ancestral origin of at least one chromosomal segment of the first user to be a birth country, a geographical region, or an ethnicity of at least two grandparents of a matching user who have a same birth country, a same geographical region, or a same ethnicity, wherein the first user and the matching user share the least one chromosomal segment, and wherein the at least one chromosomal segment comprises at least one IBD segment whose length is estimated as meeting a minimum length based on the results of the bitwise operation on the bit array;

(d) causing to display in a graphical user interface ancestral information pertaining to the ancestral origin of the at least one chromosomal segment of the first user, the ancestral information comprising a graphical representation of a karyotype of the first user, wherein the karyotype of the first user comprises one or more chromosome pairs, wherein the one or more chromosome pairs comprise the at least one chromosomal segment corresponding to the at least one IBD segment whose length is estimated as meeting the minimum length based on the results of the bitwise operation on the bit array, and wherein the ancestral origin of the at least one chromosomal segment is indicated on the at least one chromosomal segment (e) causing to display in the graphical user interface an input element for adjusting the minimum length;

(f) receiving via the input element a user input to adjust the minimum length;

(g) repeating (c) using the adjusted minimum length, wherein the at least one IBD segment's length is estimated as meeting the adjusted minimum length; and (h) causing to update in the graphical user interface the graphical representation of the karyotype of the first user, wherein the at least one chromosomal segment of the karyotype of the first user corresponds to the at least one IBD segment whose length is estimated as meeting the adjusted minimum length.

19. The computer program product of claim 18, wherein the ancestral origin of the at least one chromosomal segment is indicated by a graphical characteristic.

20. The computer program product of claim 18, wherein the ancestral information pertaining to the ancestral origin of the at least one chromosomal segment of the first user comprises a table of countries associated with the first user's ancestral origin.

21. The computer program product of claim 18, wherein the ancestral information pertaining to the ancestral origin of the at least one chromosomal segment of the first user comprises a pie chart of countries associated with the first user's ancestral origin.

22. The computer program product of claim 18, wherein the ancestral information pertaining to the ancestral origin of the at least one chromosomal segment of the first user comprises a map of countries associated with the first user's ancestral origin.

23. The system of claim 1, wherein the genetic markers comprise hundreds of thousands of genetic markers for each user.

24. The system of claim 1, further comprising displaying in the graphical user interface an element for specifying a number of required grandparents of the matching user who have the same birth country, the same geographical region, or the same ethnicity.

25. The system of claim 24, further comprising: receiving a user input specifying the number of required grandparents of the matching user; and updating the graphical representation of the karyotype of the first user to show the at least one chromosomal segment and the ancestral origin of the at least one chromosomal segment determined based on the number of required grandparents of the matching user.

* * * * *